United States Patent
Bishop et al.

(10) Patent No.: US 9,489,753 B1
(45) Date of Patent: Nov. 8, 2016

(54) RECONSTRUCTION OF THREE DIMENSIONAL MODEL OF AN OBJECT FROM SURFACE OR SLICE SCANS COMPENSATING FOR MOTION BLUR

(71) Applicant: Eyedeal Scanning, LLC, Needham, MA (US)

(72) Inventors: Robert P. Bishop, Newton, MA (US); Michael T. Sullivan, Needham, MA (US)

(73) Assignee: Eyedeal Scanning, LLC, Needham, MA (US)

( * ) Notice: Subject to any disclaimer, the term of this patent is extended or adjusted under 35 U.S.C. 154(b) by 0 days.

(21) Appl. No.: 15/213,709

(22) Filed: Jul. 19, 2016

(51) Int. Cl.
*G06K 9/00* (2006.01)
*G06T 11/00* (2006.01)

(52) U.S. Cl.
CPC .................................. *G06T 11/008* (2013.01)

(58) Field of Classification Search
USPC ......................................................... 382/131
See application file for complete search history.

(56) References Cited

U.S. PATENT DOCUMENTS

| | | | |
|---|---|---|---|
| 4,091,285 A * | 5/1978 | Logan ................... | A61B 6/4035 378/14 |
| 4,582,404 A | 4/1986 | Hamilton | |
| 4,761,071 A | 8/1988 | Baron | |
| 5,321,501 A | 6/1994 | Swanson et al. | |
| 5,491,524 A | 2/1996 | Hellmuth et al. | |
| 5,493,109 A | 2/1996 | Wei et al. | |
| 5,512,965 A | 4/1996 | Snook | |
| 5,521,657 A | 5/1996 | Klopotek | |
| 6,741,359 B2 | 5/2004 | Wei et al. | |
| 7,237,898 B1 | 7/2007 | Hohla et al. | |
| 2004/0008819 A1* | 1/2004 | Drummond ............ | A61B 6/032 378/162 |
| 2004/0066489 A1 | 4/2004 | Benedikt et al. | |
| 2005/0226366 A1* | 10/2005 | Hsieh ..................... | A61B 6/032 378/16 |
| 2006/0004291 A1* | 1/2006 | Heimdal .................. | A61B 8/08 600/459 |
| 2006/0158612 A1 | 7/2006 | Polland et al. | |
| 2006/0210122 A1 | 9/2006 | Cleveland et al. | |
| 2007/0031028 A1* | 2/2007 | Vetter ................. | G06K 9/00208 382/154 |
| 2007/0055222 A1 | 3/2007 | Hohla et al. | |
| 2007/0167784 A1* | 7/2007 | Shekhar ................. | A61B 6/032 600/443 |
| 2009/0190093 A1 | 7/2009 | Tanassi et al. | |
| 2011/0037942 A1 | 2/2011 | Lieberman et al. | |
| 2012/0018828 A1 | 1/2012 | Shao | |
| 2012/0182522 A1 | 7/2012 | Frey et al. | |

FOREIGN PATENT DOCUMENTS

| | | |
|---|---|---|
| CN | 1553783 | 12/2004 |
| CN | 1604753 | 4/2005 |
| WO | WO 93/21818 | 11/1993 |
| WO | WO 93/21818 A1 | 11/1993 |

OTHER PUBLICATIONS

PCT/US2012/060631 International Search Report and Written Opinion.

* cited by examiner

*Primary Examiner* — Gregory F Cunningham
(74) *Attorney, Agent, or Firm* — Cesari and McKenna, LLP

(57) ABSTRACT

Techniques for creating a three dimensional model of an object and eliminate artifacts due to object motion. Such techniques are applied to line scans and slice scans of an object.

20 Claims, 34 Drawing Sheets

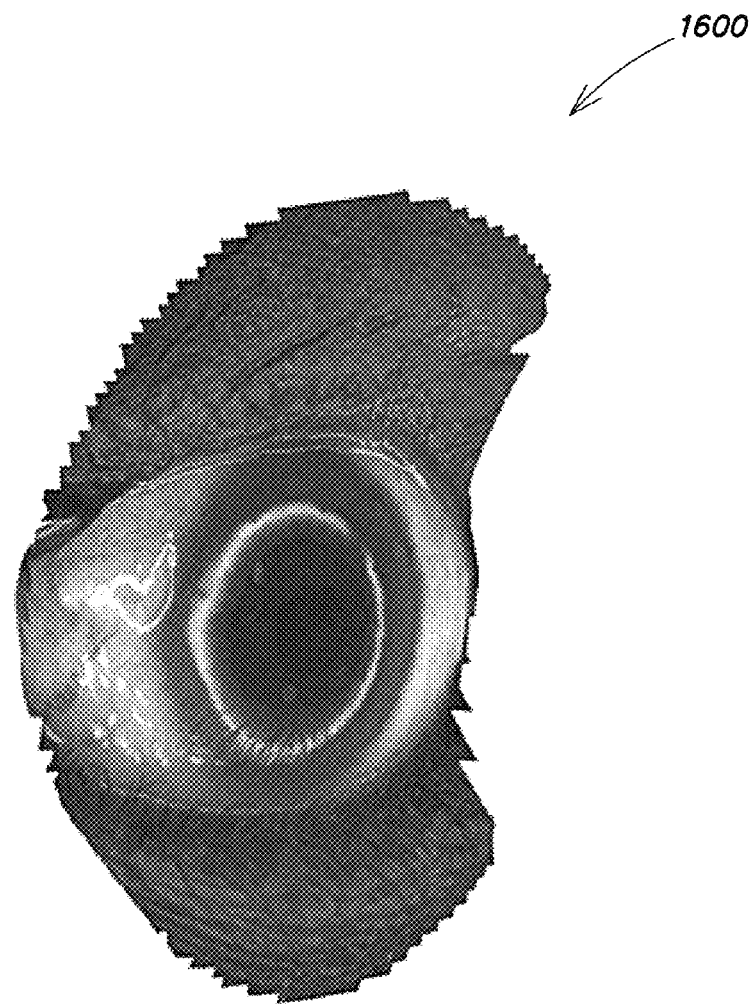
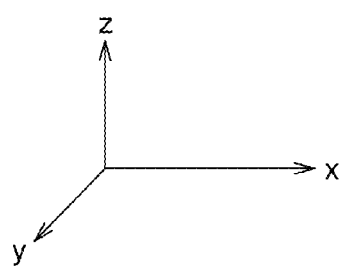
FIG. 16

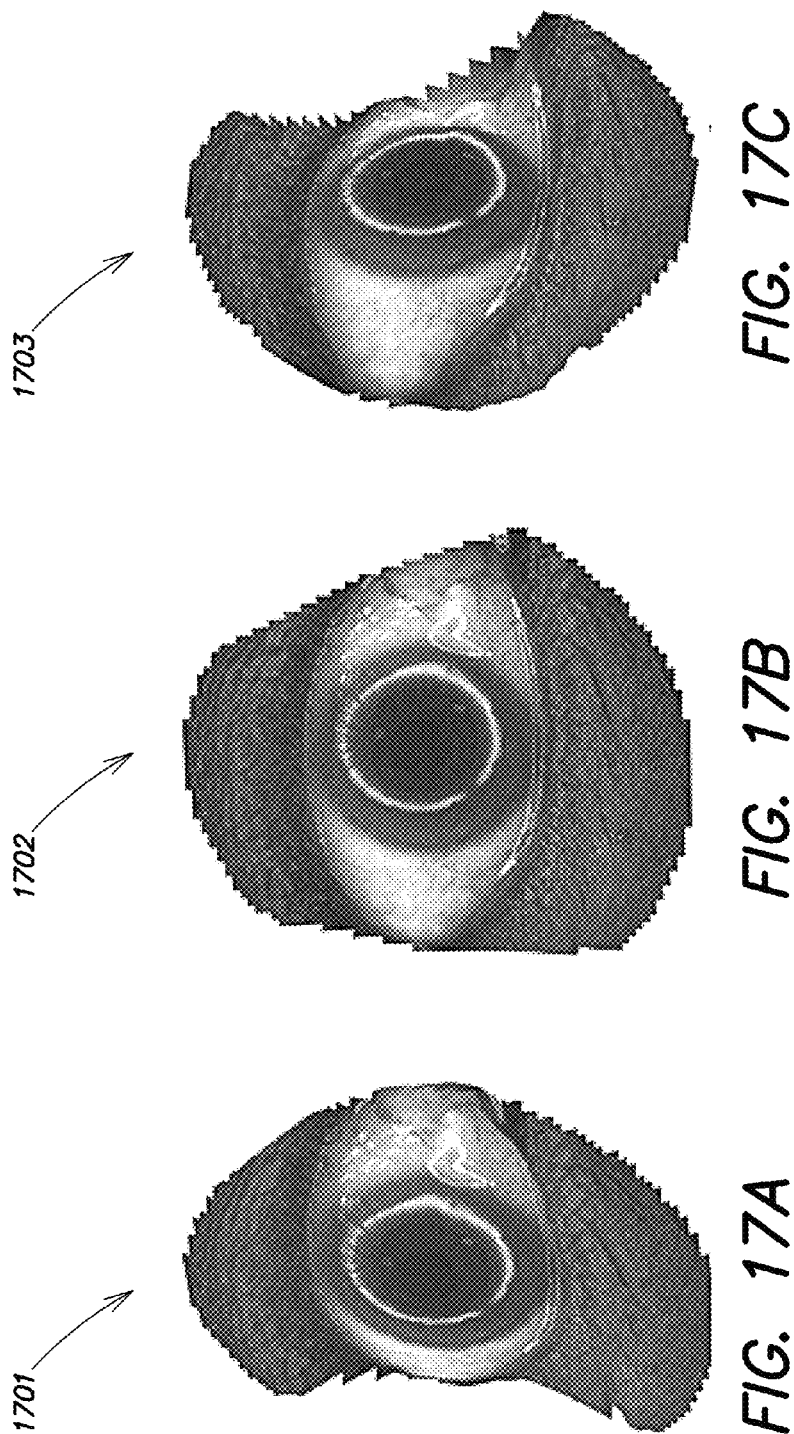

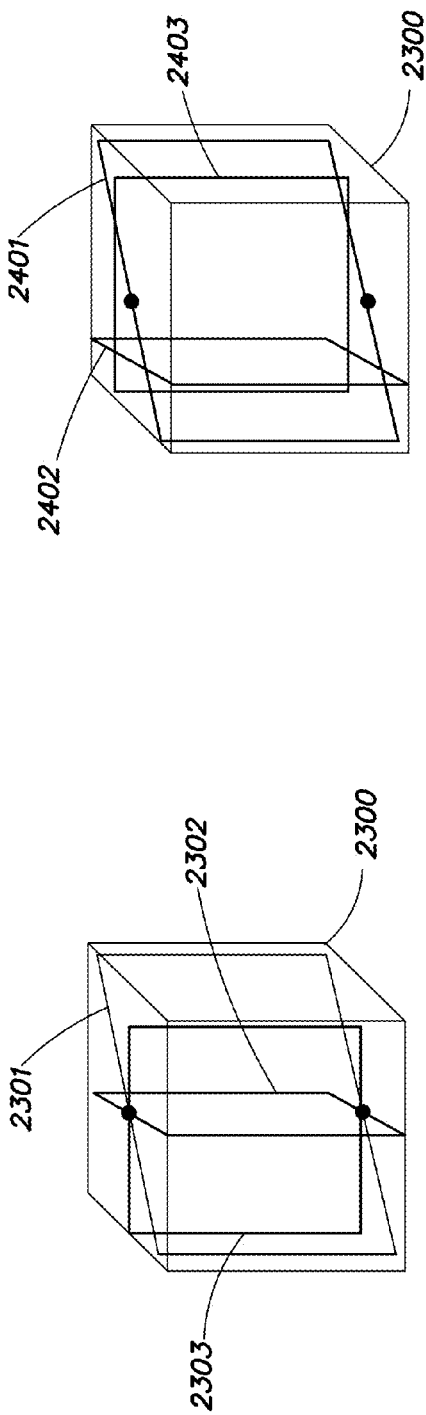
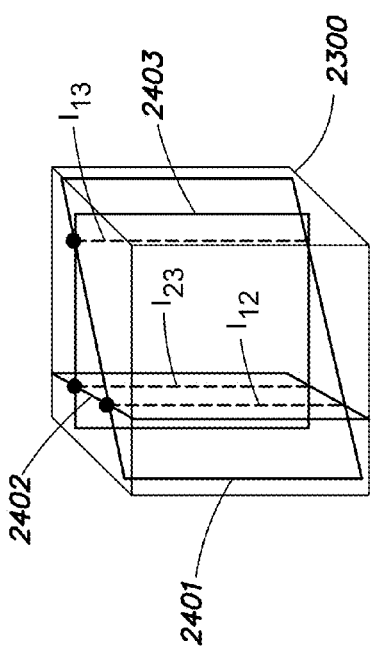
FIG. 23A
FIG. 23B
FIG. 24

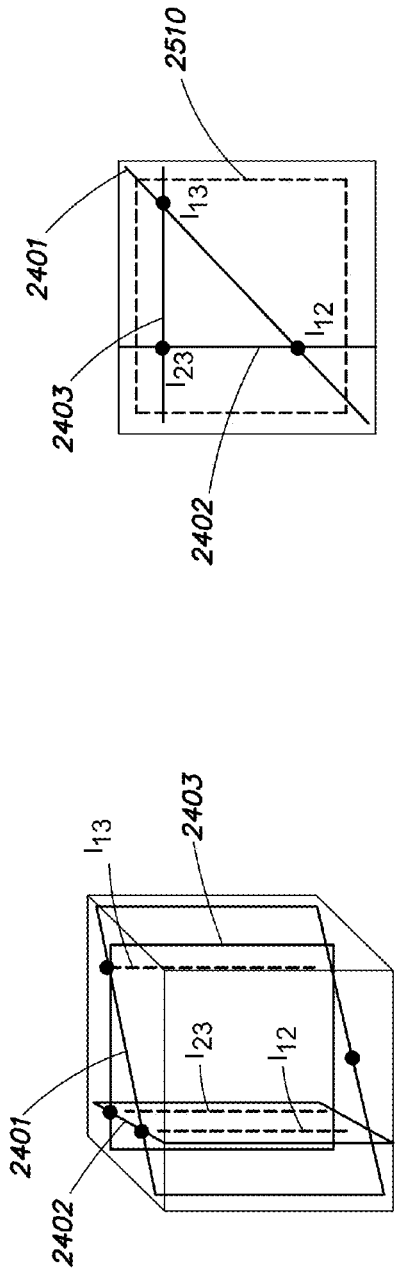
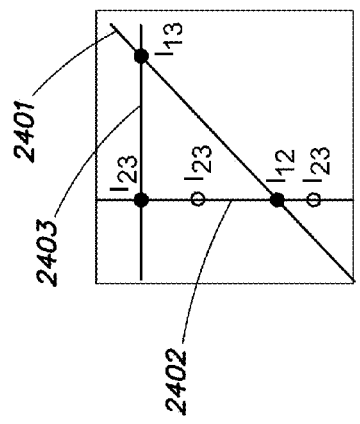
FIG. 25
FIG. 26
FIG. 27

RECONSTRUCTION OF THREE DIMENSIONAL MODEL OF AN OBJECT FROM SURFACE OR SLICE SCANS COMPENSATING FOR MOTION BLUR

BACKGROUND

Technical Field

This application relates to imaging of objects in three dimensions, and more particularly to compensating for motion blur.

Background Information

There are numerous scanning technologies in which multiple line scans or image slices are combined to reconstruct the three dimensional shape of an object. Such scanning technologies include: (a) Laser triangulation, to create surface line scans of an object, as used for example in surface CAD-CAM reconstruction applications, and (b) Optical Coherent Tomography (OCT), Magnetic Resonance Imaging (MRI), Ultrasound Imaging, Radar imaging, and Sonar Imaging, to create image slice scans of an object for internal object 3D reconstruction applications. In all of these applications multiple individual scan lines or image slices must be recombined, with precise knowledge of the spatial relationship between each scan line or image slice, to accurately reconstruct the object in three dimensional space.

Examples of such image slices are shown in FIGS. 1 to 3. FIG. 1 shows example MRI image slices 100 of the human brain. FIG. 2 illustrates a single OCT scan slice 200 of the human eye. FIG. 3 is an example single ultrasound scan slice 300 of the human abdominal area.

SUMMARY

Motion of the object during or between acquisition of the multiple scans or slices introduces severe artifacts in the reconstructed three dimensional image. For example, consider the stationary stair case object 400 shown in FIG. 4 and the flat object 500 in vertical motion shown in FIG. 5. When the stationary stair case object of FIG. 4 is scanned using any of the above listed technologies the measurement device will correctly indicate that the object has a step with a height difference of "h". However, if the flat object 500 shown in FIG. 5 moves a vertical distance h between successive scans, the measurement device will incorrectly indicate that there exists a step in the surface of height "h" when the surface 502 is perfectly flat but in motion as shown by arrow 510. Thus the object 400 of FIG. 4 may not be distinguished from the object 500 in FIG. 5.

FIGS. 6A and 6B are images of a human eye being scanned. FIGS. 6A and 6B show the x,y path of a scan line at different spatial positions during the scan. FIG. 6A is a first image 600 showing scan 610 taken at time t=0. The "ring" 620 around the pupil is an artifact of reflection of a white light illuminator in the scanner. FIG. 6B is the 25$^{th}$ image 650 showing scan 660, taken at time t=0.65 seconds. Image 700 in FIG. 7 is the superposition of FIGS. 6A and 6B showing how much the eye 730 moved in the x and y directions due to random eye motion within the 0.65 second scanning period.

While FIG. 7 shows how much the eye moves in a plane parallel to the camera, the camera cannot detect vertical displacement perpendicular to the camera in the z direction. In fact, if the vertical displacement lies within the depth of field of the camera optics, the vertical motion may not even be detectable, because the image will remain in focus. FIG. 8 shows an example of this situation; since the object moves along the same axis 810 as the camera lens 805 depth of field 820, motion of the object 800 may not be evident between successive scans.

A summary of various embodiments is provided below. Detailed explanations of the various embodiments with reference figures is presented in the section entitled "Detailed Description of an Illustrative Embodiment".

In one example embodiment, these problems are overcome by an apparatus and/or method that includes a camera directed along an imaging axis. The camera generates a sequence of two-dimensional images of the object including a distinct visual feature. A scanner also generates multiple scans of the object, each scan including a plurality of sampled measurements of the object. Each scan should have a corresponding two dimensional image. Some type of fixed or otherwise determined spatial relationship is maintained between the scanner and the camera.

A controller, such as a programmable digital computer or digital signal processor, is connected to control the camera and the scanner and to process their outputs. The controller controls the scanner to produce a plurality of scan lines, each scan line including a plurality of sampled measurements. The scanner is furthermore controlled such that each of the scan lines intersects at least one other scan line in an image plane observed by the camera, to thereby create a path from any single scan line to any other scan line in the image plane. The controller also captures an image of the object including the distinct visual feature from the camera for each of the plurality of scan lines, thereby capturing a corresponding image for each scan line. The captured images are then aligned by overlaying the distinct visual feature, to thereby also align the corresponding scan lines in the image plane by a corresponding amount.

The individual sampled measurements for each given scan line are then connected to produce a continuous representation of each scan line in three dimensional space. For at least one set of two scan lines, the controller then locates a point in the image plane where the continuous representations of the two scan lines cross, and then moves at least one scan line along the imaging axis in a plane perpendicular to the image plane. This results in the two continuous scan line representations intersecting at a common point in three dimensional space, thereby compensating for movement of the object between successive scans of the scanner.

A three dimensional representation of the object may then be generated from two or more of the intersecting continuous scan line representations.

In some implementations, the captured image may be a two-dimensional image of a surface of the object containing the distinct visual feature.

The scanner may be of different types. In one implementation, the scanner is a surface height scanner and the sampled measurements each correspond to a height determined from a distance between a reference point to the object at a selected position along the scan line.

In an other implementation, the scanner is a slice scanner, and the sampled measurements are slice scans. In this implementation, a surface of the object is extracted from each slice scan. Example slice scanners include OCT, CAT, Ultrasound, MIR, sonar, or radar.

In a preferred embodiment, a time to acquire the sampled measurements from the scanner is sufficiently small such that motion blur occurring during the sampling of a scan line or slice scan can be ignored.

In other aspects, an apparatus and/or method generates a three dimensional representation of an object using a scanner for generating slice scans. Each slice scan includes an array of samples in two dimensions, with each sample representing an intensity of a detected physical property of the object. A controller, such as a programmable digital computer or digital signal processor, is connected to the scanner. The controller controls the scanner to produce a plurality of slice scans, with the slice scans being arranged such that each slice scan intersects at least two other slice scans, even as the object moves between successive slice scans. The controller also controls the slice scans to intersect such that a continuous path exists from each slice scan to any other slice scan. The controller processes the output of the scanner to locate a set of common intensity values that a given scan slice has in common with a selected intersecting slice, and then aligns the intensity values that the given slice and selected intersecting slice have in common. This then fixes a position for the given scan slice and selected intersecting slice in a three dimensional representation of the object.

In this embodiment, the controller may further process the output of the scanner to locate two or more sets of common intensity values that the given slice has in common with the selected slice. Using relative position information for the given slice with respect to a third slice, the controller may then determine which one of the two or more sets of common intensity values to use to fix the position of the given scan slice and the selected intersecting slice.

In other optional implementations, the control may further limit a size and location of a search area within which to locate intersecting slices, using (a) slice scan angle and slice position and (b) a known maximum rate of object motion between scan slices.

In this implementation, a time to acquire the samples may also be sufficiently small such that motion blur occurring during successive samples of a slice scan can be ignored.

BRIEF DESCRIPTION OF THE DRAWINGS

The description below refers to the accompanying drawings, of which:

FIG. 16 is a three dimensional model of a human eye;
FIGS. 17A, 17B and 17C are representations of rotational views of the model of FIG. 16;
FIG. 23A shows intersecting slice scans when the object does not move during the scan.
FIG. 23B shows the intersecting scan slices when the object does move during the scan;
FIG. 24 illustrates how the slices may share a common set of intensity values;
FIG. 25 illustrates a spatial region over which the slices must intersect in 3 dimensions;
FIG. 26 illustrates a spatial region over which the slices must intersect in 2 dimensions;
FIG. 27 shows a case of duplicate intensity vectors where it is not yet known where the slices are connected.

DETAILED DESCRIPTION OF AN ILLUSTRATIVE EMBODIMENT

Described herein are various apparatus and methods for removing three dimensional (3D) motion blur in line scan and slice scan images. The techniques enable the 3D shape of an object to be reconstructed without adverse effects due to motion in x, y, and z directions as the object is scanned.

Implementation 1

Figure 9:
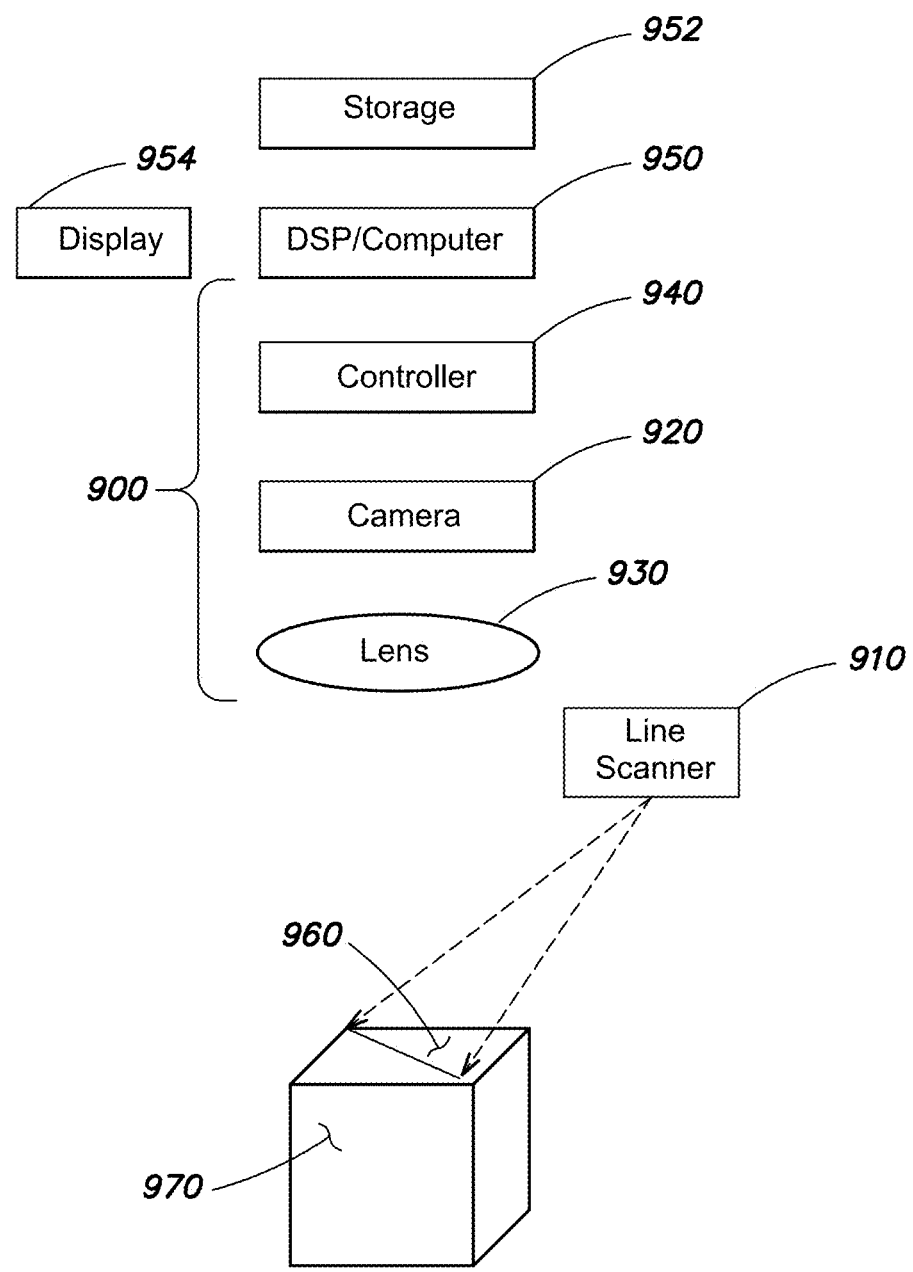
FIG. 9 is an example implementation.

Three Dimensional Reconstruction of Line Scanned Objects and Elimination of Motion Blur This first implementation (Implementation 1) uses a line scan device to obtain a 3D model. Referring to FIG. 9, this requires the following equipment and operations:

1. A single two dimensional (2D) camera 920 to take a sequence of images of object 970 which includes at least one feature on the surface 960 of object 970. The camera may be a television camera or other digital camera capable of capturing a sequence of images.

2. A scanner 910 that measures at least the distance to the surface of the object 970 along a sequence of line scans (e.g., 960) (such as a triangulation sensor).

3. The scanner is controlled by a controller 940 such that scan lines must intersect in such a way as to create a path to travel from any single scan line to any other scan line.

4. A determined spatial relationship exists between the camera 920 and line scan 910 device. The determined spatial relationship may be fixed by mounting the camera and scanner on a shared platform. In other arrangements, the scanner and camera may move with respect to one another, but the spacing between them follows a known pattern.

5. The time required to scan a single line is sufficiently fast such that no motion blur occurs during a single scan line acquisition time or the motion blur is significantly small such that it can be ignored over the line scan time.

6. A digital signal processor and/or computer 950 is programmed to process the output of the camera 920 and the output of the scanner 910, and interacts with controller 940, to control the operation of the camera, the scanner, and to perform the method steps below. The DSP/computer 950 may further include storage 952, display 954 and other peripheral components known in the art.

Given the above requirements are satisfied, the surface 960 of object 970 can be reconstructed in three dimensional space by a line scan device. Please refer to the method steps illustrated in FIGS. 10A to 10D as follows.

Step 1 (FIG. 10A): Take at least two surface line scans, scan 1 (1010-1) and scan P (1010-P), and also capture a corresponding image of the surface with the camera, simultaneously with each scan; store the line scan and camera image data for further processing. Select at least one feature (1020-1, 1020-P) in the surface image of the object to be used for x and y alignment of the surface height line scans. This example uses a "+" sign as the alignment feature.

Step 2A (FIG. 10B): Move one surface image relative to the other surface image in x and y to overlay the alignment feature (1020-1, 1020-P) present in both images. Also move the surface height line scan an identical amount as the surface image to maintain at all times the precise spatial relationship between the alignment feature in the surface image and each surface height line scan.

Step 2B (FIG. 10B): Mathematically connect the individual sampled height data points in each line scan as shown by the bold lines on the top surface of the object. One way to connect the points is to fit a polynomial to the sampled data values, 1010-1 and 1010-P respectively. Locate the x, y coordinate on the top surface that is common to both line scans 1(1010-1) and P (1010-P). This is the coordinate where the two scans intersect in the x-y plane, as indicated by dashed vertical line V1.

Step 3 (FIG. 10B): Since the common x, y data point lies on the surface of the object, and there is one and only one top surface, both surface height line scans must have the same z height value relative to the object where the two scans intersect in the x, y plane as indicated by vertical line V1 in Step 2B. Therefore line scan P (1010-P) can be and is connected to line scan 1 (1010-1) at this surface x, y, z coordinate.

Step 4 (FIG. 10C): For each subsequent line scan 1010-N acquired of the object (referred to as scan line N) the alignment feature 1020-N is located in the accompanying surface image. This is true whether the object is moving or stationary as it is being scanned.

Step 5 (FIG. 10D): Mathematically connect the individual sampled data points in scan line N using the same procedure described in step 2B. Find which previously processed line scan number, referred to as line scan P, that line scan N intersects. Locate the x, y coordinate that is common to line scan N and P. This is the x, y coordinate where the two scans intersect in the x-y plane, as indicated by dashed vertical line V2.

Step 6 (FIG. 10D): At the intersecting x, y surface coordinate common to line scans N and P (indicted by vertical line V2 in FIG. 10D (Step 5)), connect the line scans in the vertical direction such that line scan N will now have the same x, y, z coordinate value as line scan P where the two line scans intersect.

Continue the operations in steps 4, 5, and 6 until all intersecting scan lines have been connected in the vertical Z height axis.

Figures 10A, 10B, 10C, 10D:
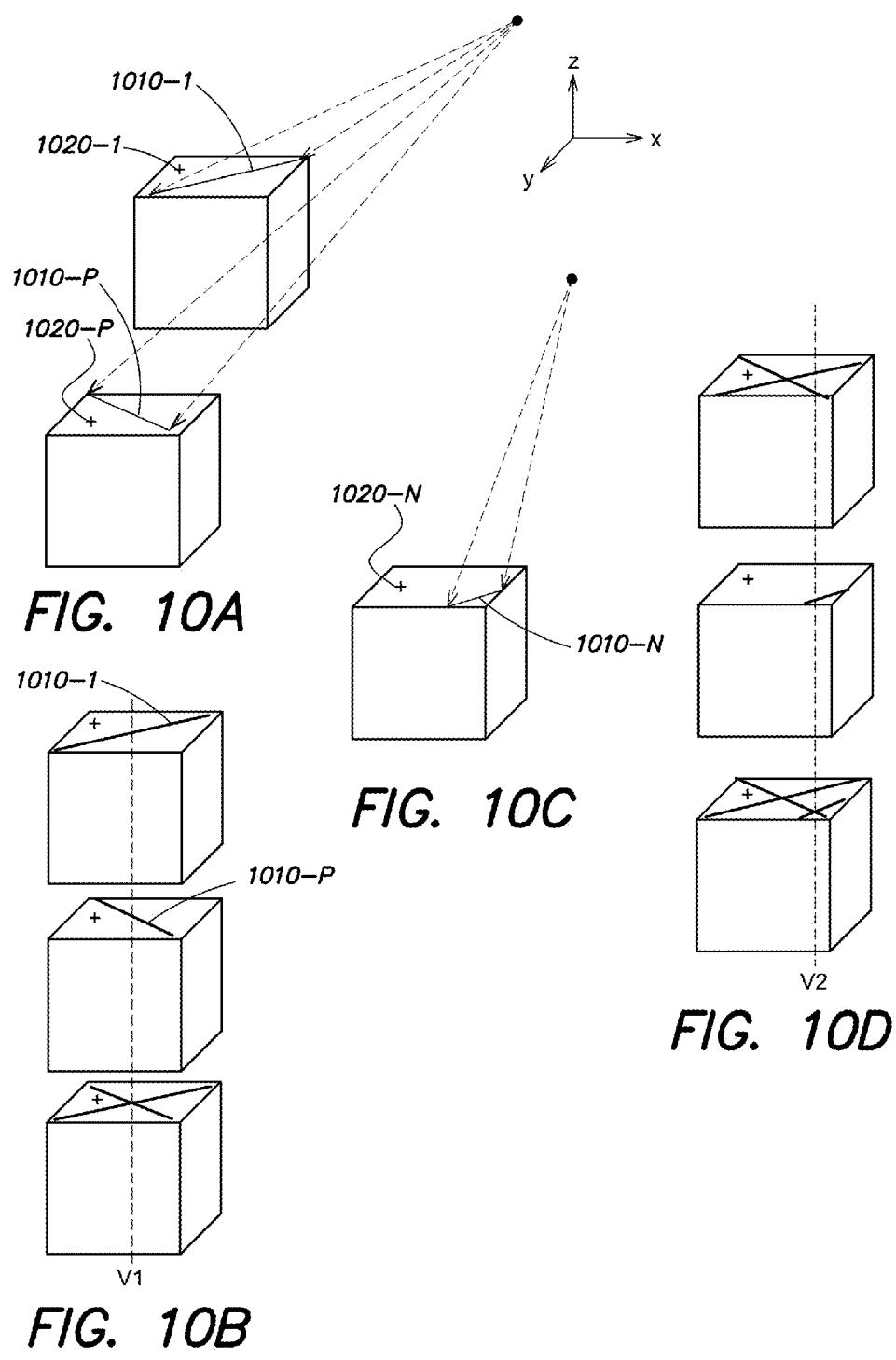
FIGS. 10A to 10D illustrate a sequence of steps to perform a three dimensional (3D) reconstruction of line-scanned objects with motion blur eliminated.
Figure 11A:
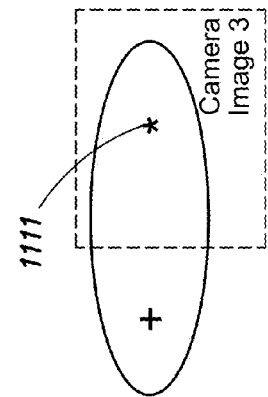
FIGS. 11A through 11C are an example of using multiple alignment features for aligning images and scans.
Figure 11B:
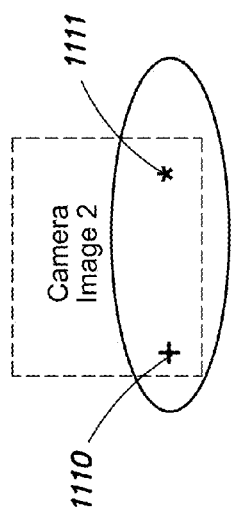
Figure 11C:
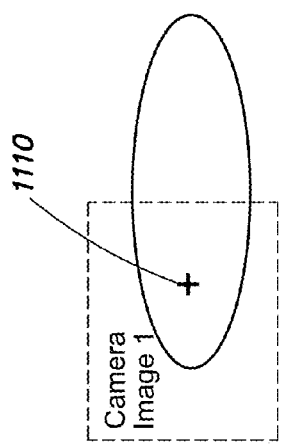

While FIGS. 10A through 10D illustrate the use of one alignment feature in the camera image to spatially align the object in the x,y camera plane between two scans; it may be necessary or useful to use multiple features on the object surface to achieve alignment, especially if a single feature is not present in all camera images due to object motion. FIGS. 11A,11B, and 11C show how multiple alignment features between consecutive images can be used for alignment. As an example, the "+" (plus sign 1110) is only present in the camera image of FIG. 11A. Both the "+" and "*" (asterisk 1111) are present in camera image of FIG. 11B and only the "*" asterisk is present in the camera image of FIG. 11C. In this example the "+" sign can be used to align FIG. 11A to 11B and the "*" asterisk can be used to align FIG. 11B to FIG. 11C. This by default aligns FIG. 11A to FIG. 11C even though they do not share a common feature. In this manner all images and scans can be aligned to each other in the x,y camera image plane. In general any one image can be aligned to any other image either by directly containing a feature common to both images or by finding pairs of common features in intermediate images linking the photos together as shown in FIGS. 11A, 11B, and 11C.

It is noted that methods for alignment of two images in the x,y plane is well known in the art. The novelty of this implementation is believed to be the complete method of line scan alignment in the z axis, to compensate for object motion between line scans.

Figure 1:
FIG. 1 is a set of MRI image slices of a human brain.
Figure 2:
FIG. 2 is a single OCT scan of a human eye.
Figure 3:
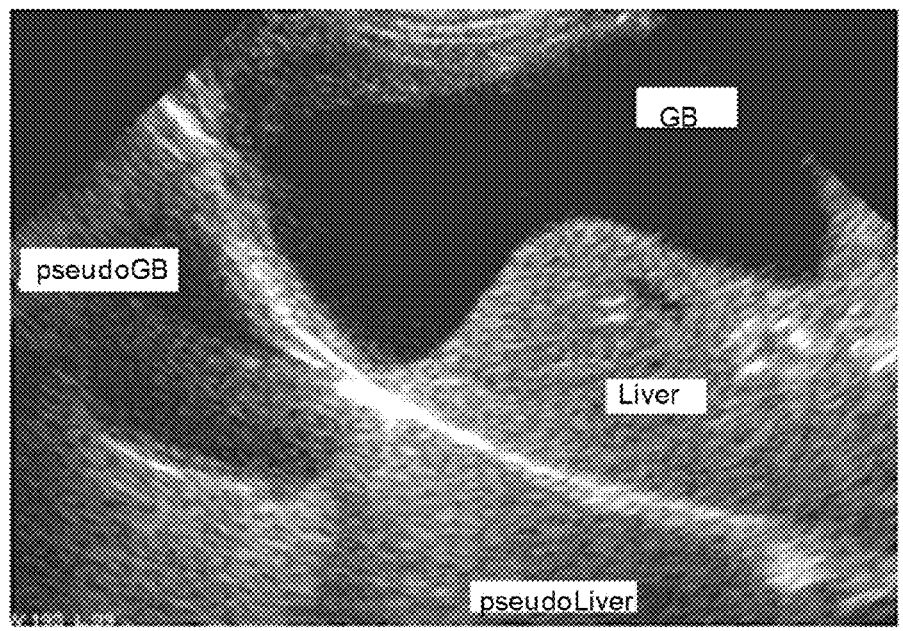
FIG. 3 is a single ultrasound scan of a human abdomen.
Figure 4:
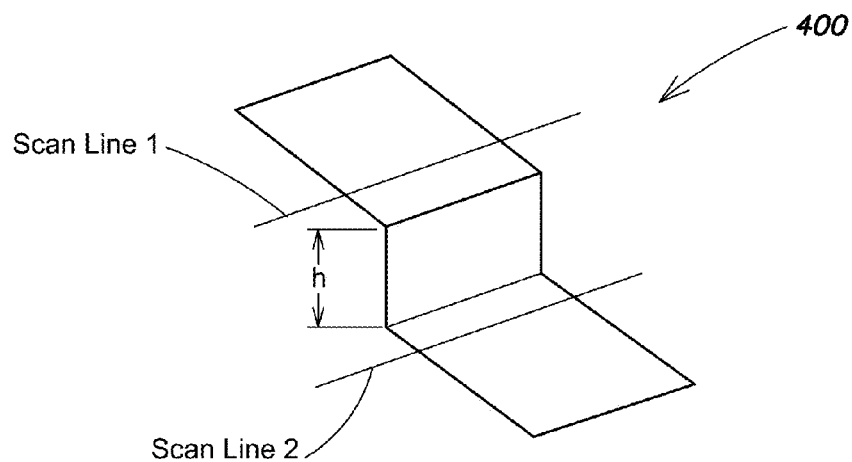
FIG. 4 is an example situation where two scans are taken of a stationary staircase object.
Figure 5:
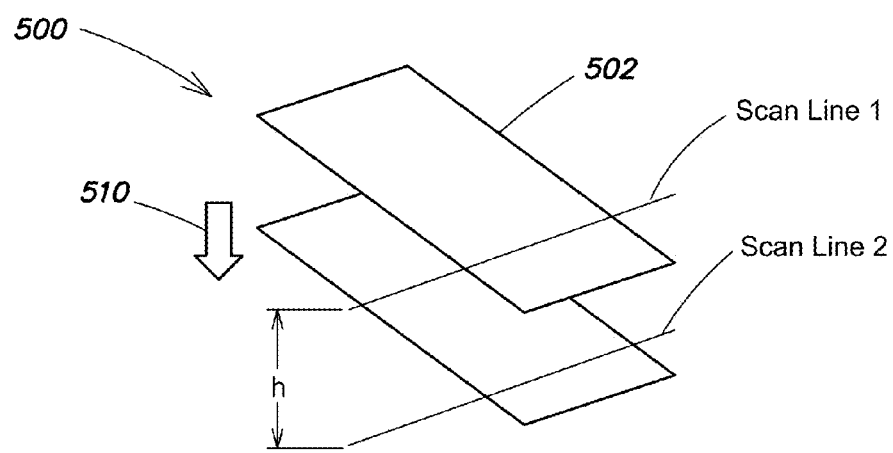
FIG. 5 is an example situation where two scans are taken of a moving flat object.
Figure 6A:
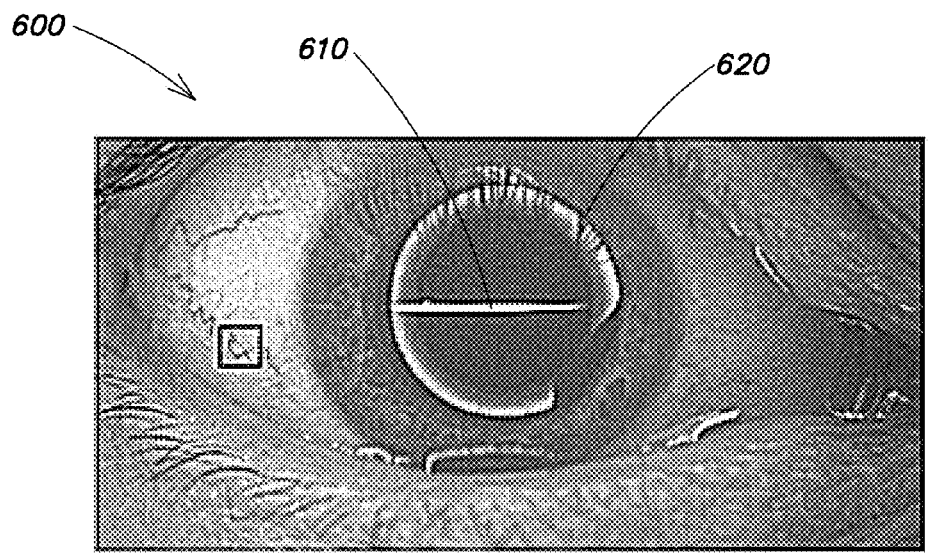
FIG. 6A is an image of an eye taken during a first scan (at time t=0 seconds)
Figure 6B:
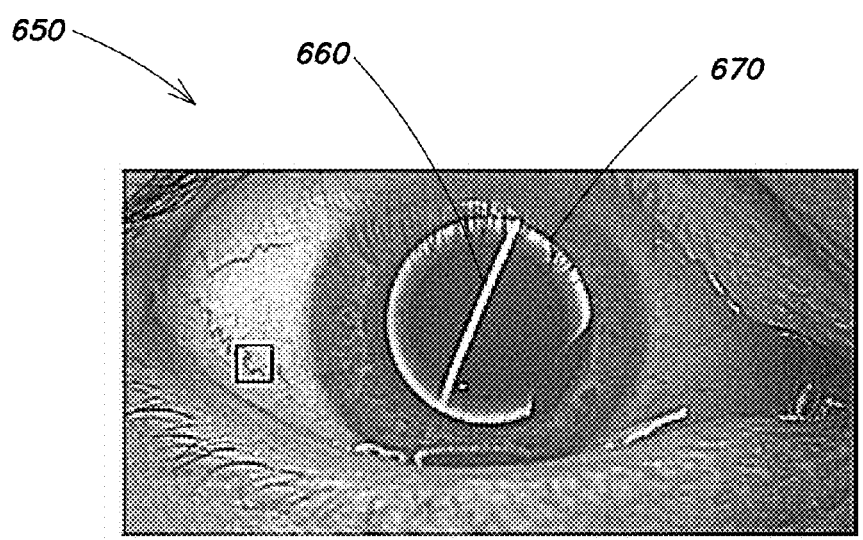
FIG. 6B is an image of the eye taken during a subsequent scan (at time t=0.65 seconds)
Figure 7:
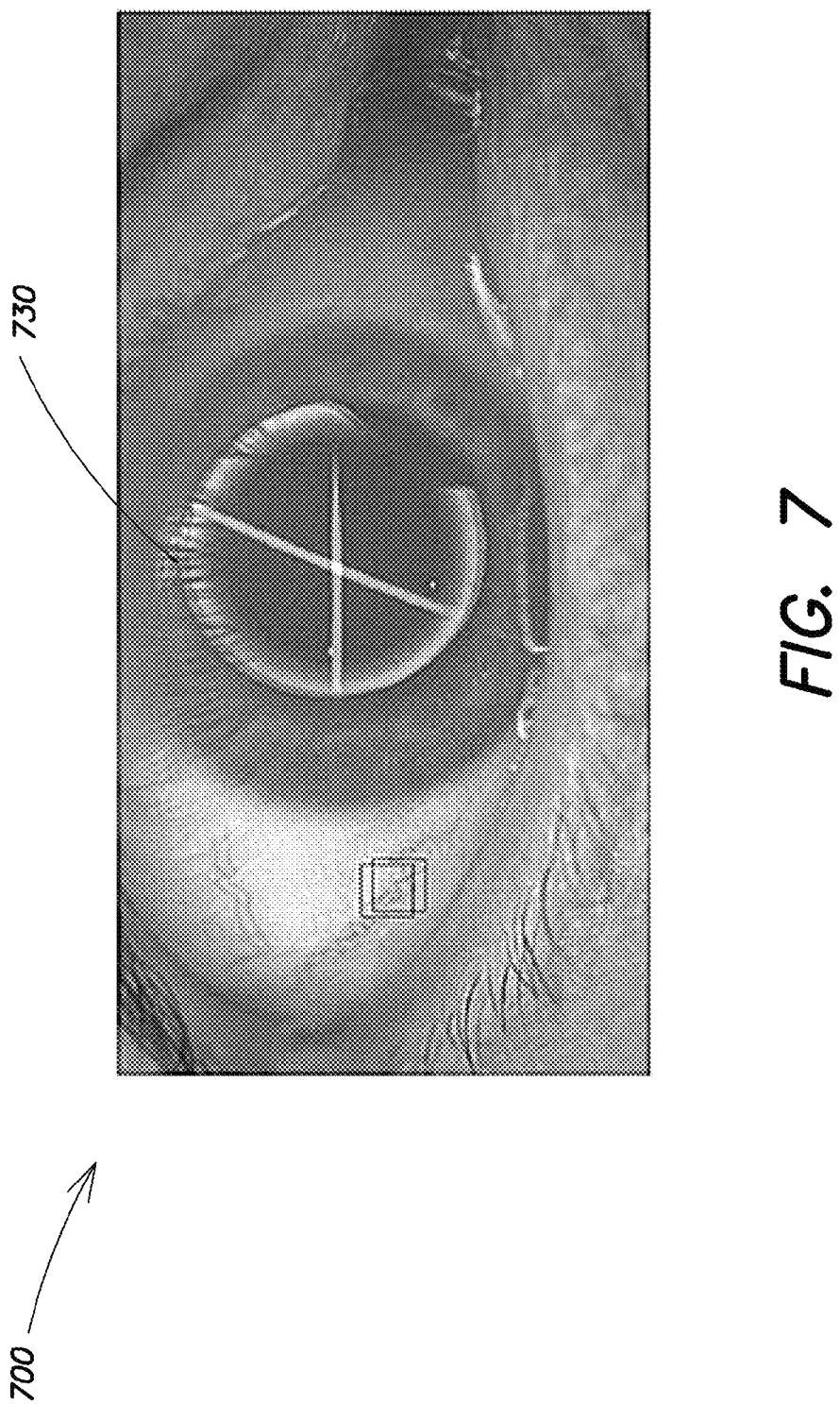
FIG. 7 is a superposition of the FIGS. 6A and 6B images.
Figure 8:
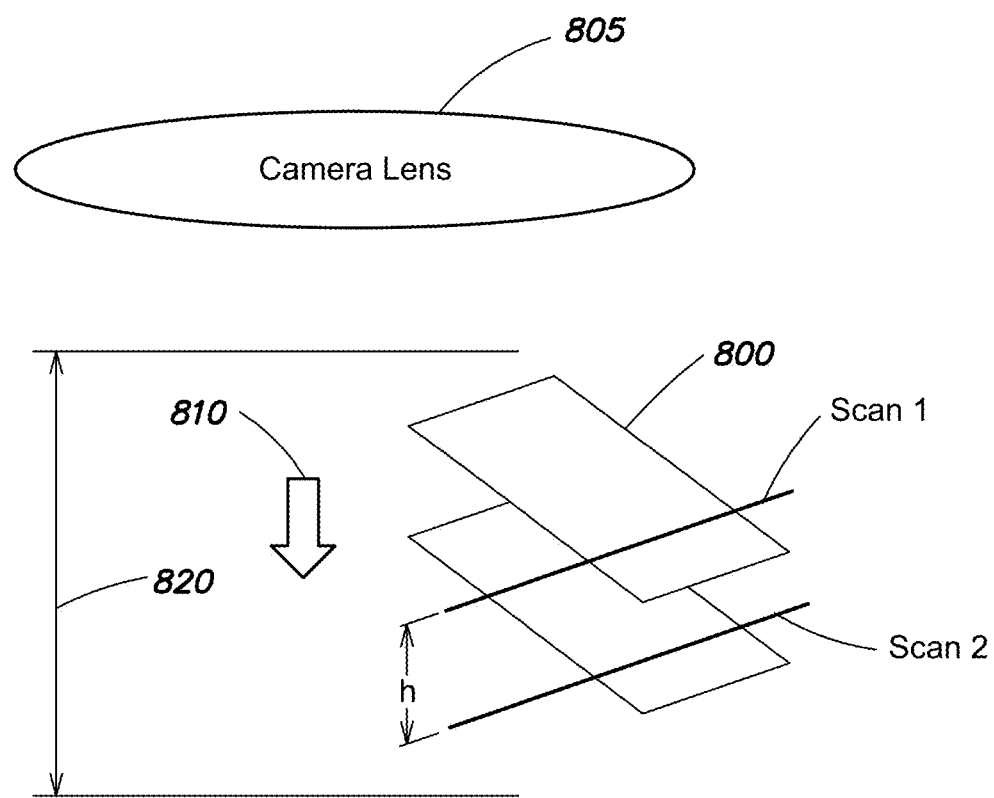
FIG. 8 shows how motion parallel to the depth of field may not be discernable by comparing images.
Figure 12A:
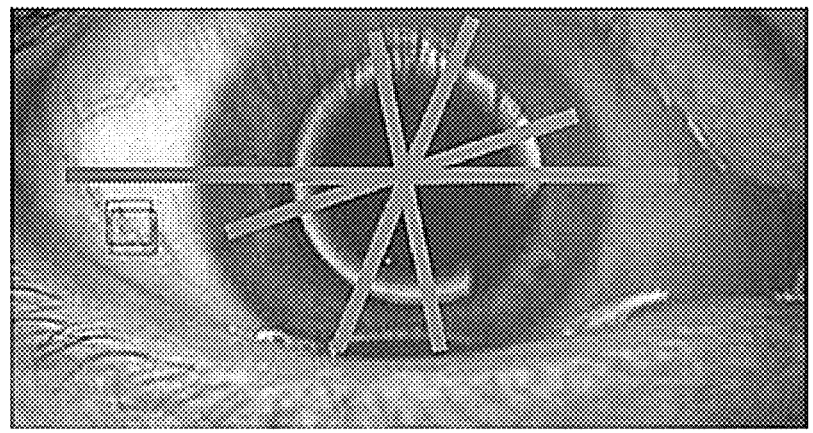
FIG. 12A is an example scan pattern prior to alignment.
Figure 12B:
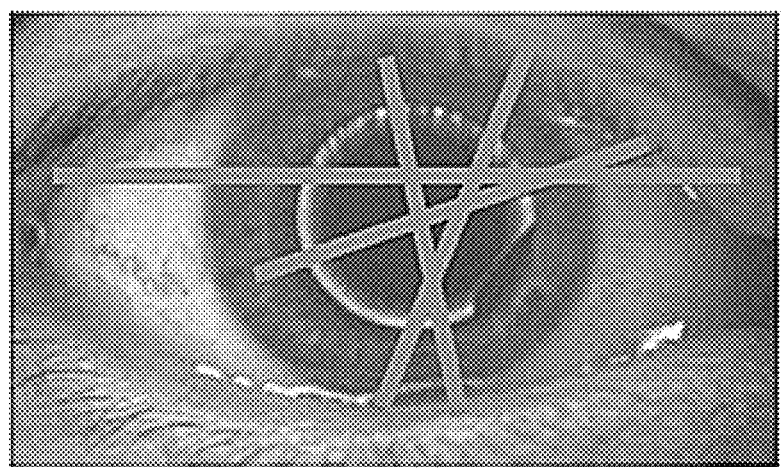
FIG. 12B is the scan pattern after alignment.
Figure 13A:
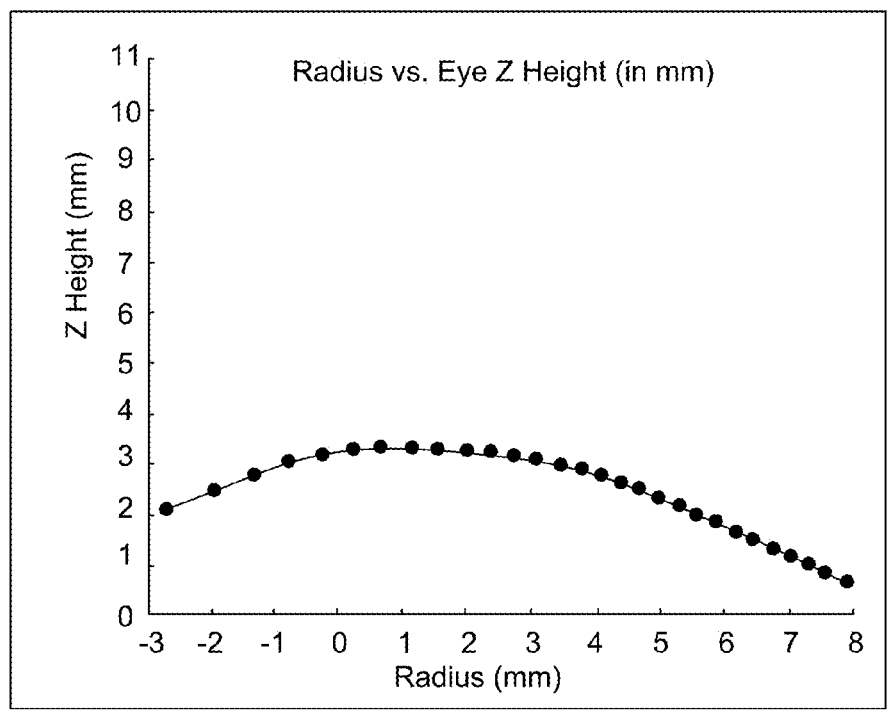
FIG. 13A shows a measured z height surface profile along the single scan line shown in FIG. 13B.
Figure 13B:
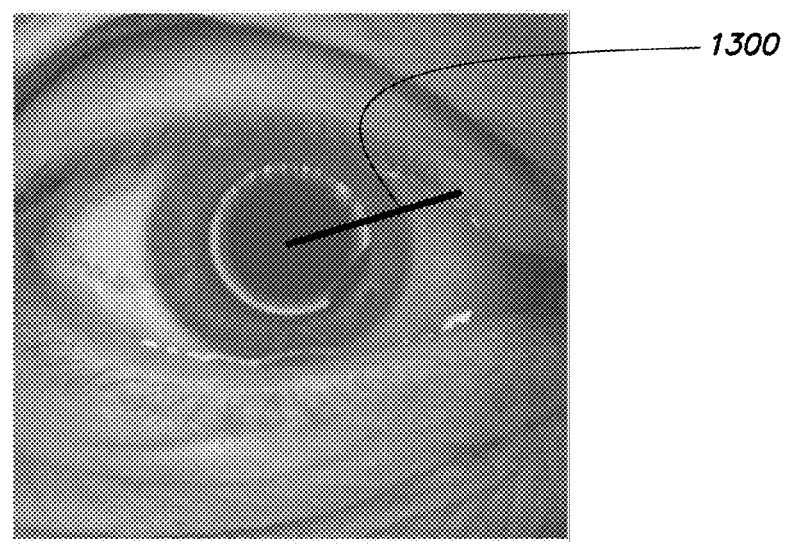

FIG. 12A is an example 1201 of multiple intersecting line scans of a human eye. The corresponding surface images are overlaid. This is the pattern prior to the x,y alignment needed to compensate for the eye motion shown in FIG. 7. FIG. 12B illustrates how the scans will be positioned relative to each other after alignment in the x, y plane 1202 using the aligned surface images per the method steps as illustrated in FIGS. 10A through 10D.

s FIG. 13A shows an example measured Z height surface profile along an example single scan line 1300; the corresponding image is in FIG. 13B.

Figure 14:
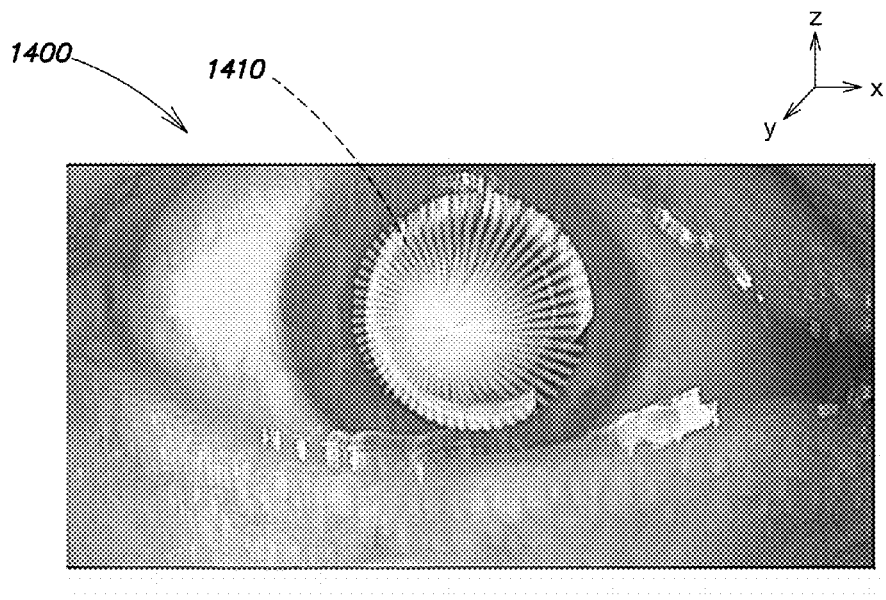
FIG. 14 is a superposition of 120 unaligned scans/images with blurred image features.
Figure 15:
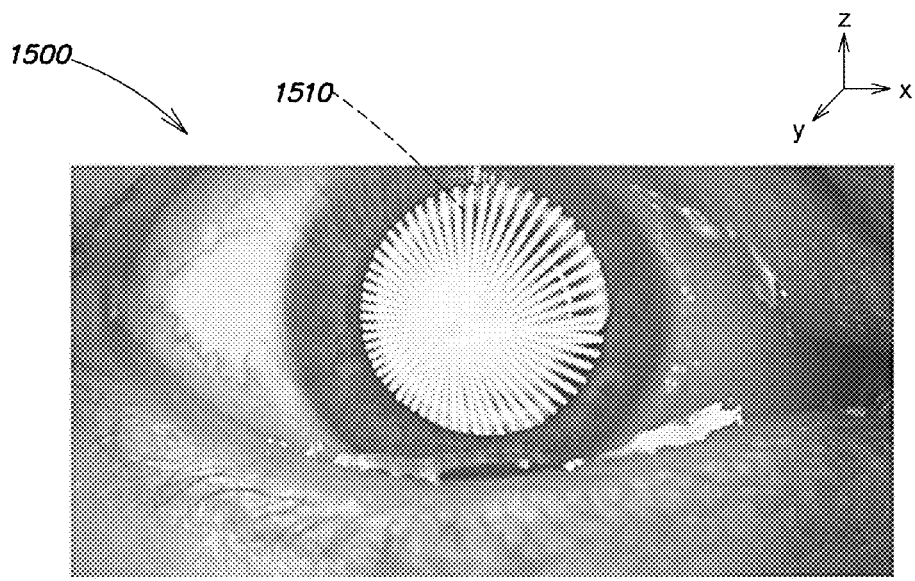
FIG. 15 is a superposition of the same 120 scans/images after alignment with sharply defined image features.

FIG. 14 is the superposition 1400 of one-hundred twenty (120) unaligned scan images of an eye acquired over a 3 second total scan period with each image having a corresponding Z height scan line profile. FIG. 14 shows the actual scan pattern 1410 and density of data points over the pupil of the eye. Note that the features in FIG. 14 are blurred. FIG. 15 shows the superposition 1500 of the 120 scans/images 1510 after alignment eliminating motion blur in the x and y directions using the methods described in FIGS. 10A to 10D. Note that the features in FIG. 15 are sharp.

In another scan of the eye, the 120 intersecting scan lines shown in FIG. 14 were radially extended past the eyelids and the three dimensional model of the eye shown in FIG. 16 was created using the reconstruction methods described in FIGS. 10A to 10D, to compensate for motion in the Z direction.

The three dimensional model can be rotated on the computer screen 954 (See FIG. 9) to display the model at different desired viewing angles 1701, 1702, 1703 as shown in FIGS. 17A to 17C.

Implementation 2
Three Dimensional Reconstruction from Slice Scans of an Object and Elimination of Motion Blur This implementation describes methods for three dimensional reconstruction from slice scans of an object and elimination of motion blur. Slice scans create image slices of an object. Scanning technologies such as: Optical Coherent Tomography (OCT), Magnetic Resonance Imaging (MRI), Ultrasound Imaging, Radar imaging, and Sonar Imaging may be used to create image slices of the object. For each of these applications, the multiple individual image slices must be recombined, with precise knowledge of the spatial relationship between each slice and the object being scanned, to reconstruct the object in three dimensional space.

Figures 18A, 18B:
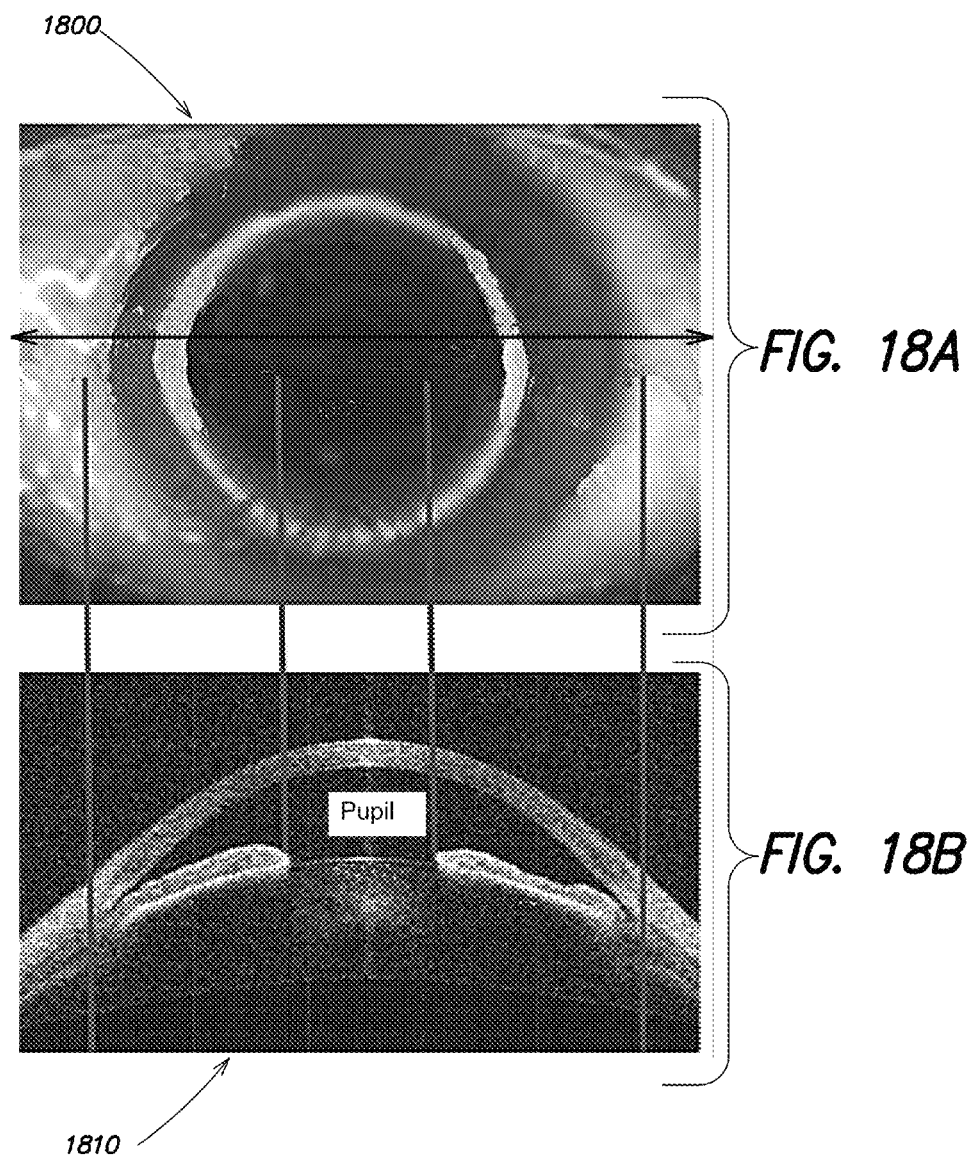
FIG. 18A is an image of an eye.
FIG. 18B is an OCT scan slice of the same eye as in FIG. 18A.

To describe this novel 3D object reconstruction algorithm, (Implementation 2) we will use OCT scans of the eye as an example. FIG. 18A is an image 1800 of an eye showing the relative position of an example OCT scan slice across the eye; and FIG. 18B is an example Optical Coherent Tomography (OCT) image slice 1810 of the eye.

Figure 19:
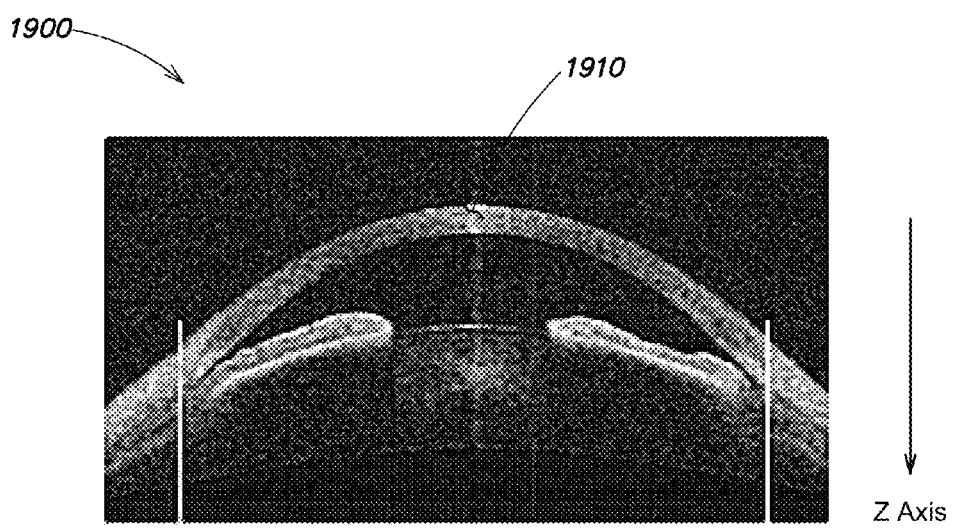
FIG. 19 shows how the top surface of the eye can be identified.

The top surface of the object (eye) can be easily identified in each image slice 1900 as shown in FIG. 19 such as by identifying the "first" high contrast boundary 1910 encountered when moving "down" in the z axis direction. Once the top surface is identified the object can be reconstructed in three dimensional space using the method steps described in FIGS. 21A through 21D, given the image slices meet the criteria set forth below.

Figure 20:
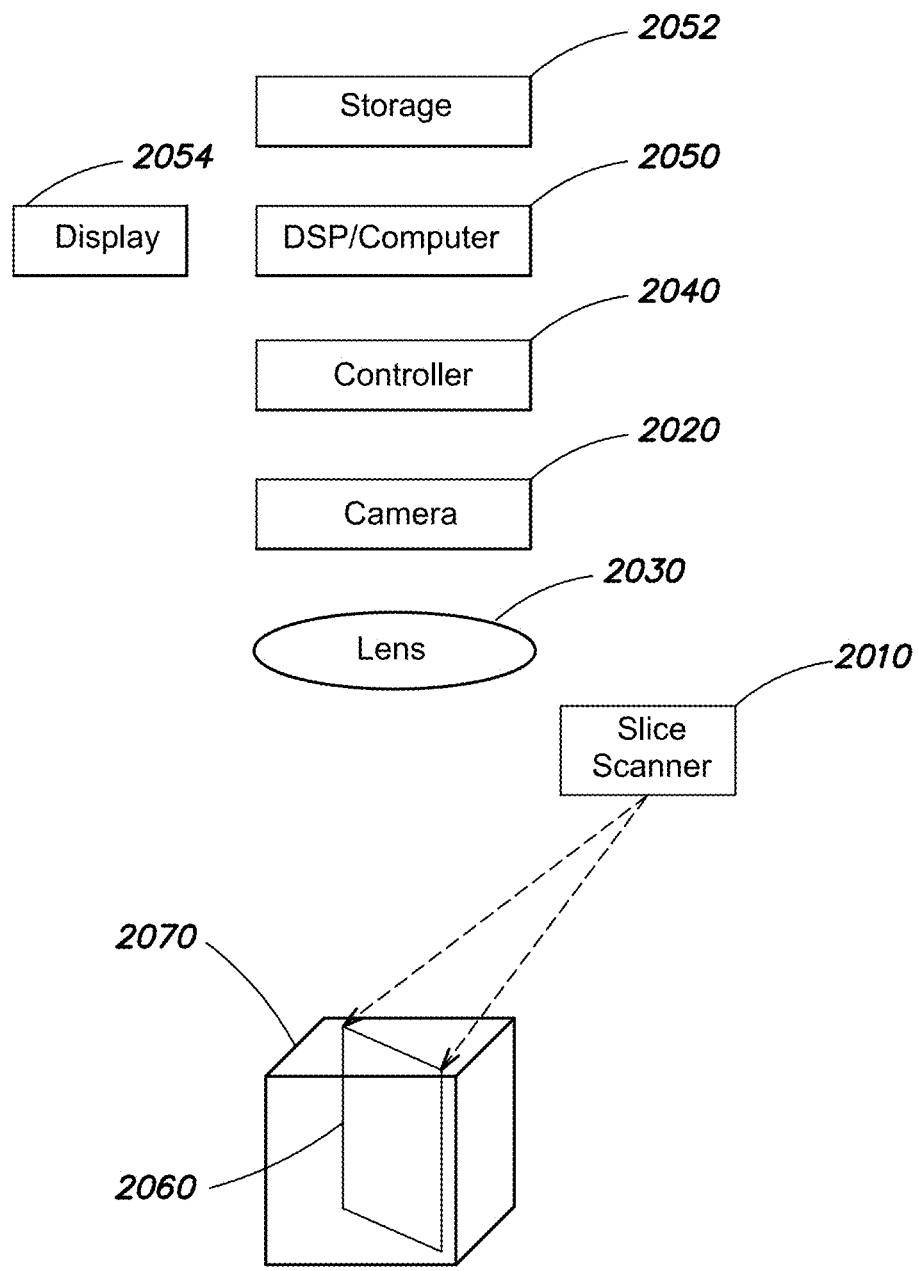
FIG. 20 shows a second implementation.
Figures 21A, 21B, 21C, 21D:
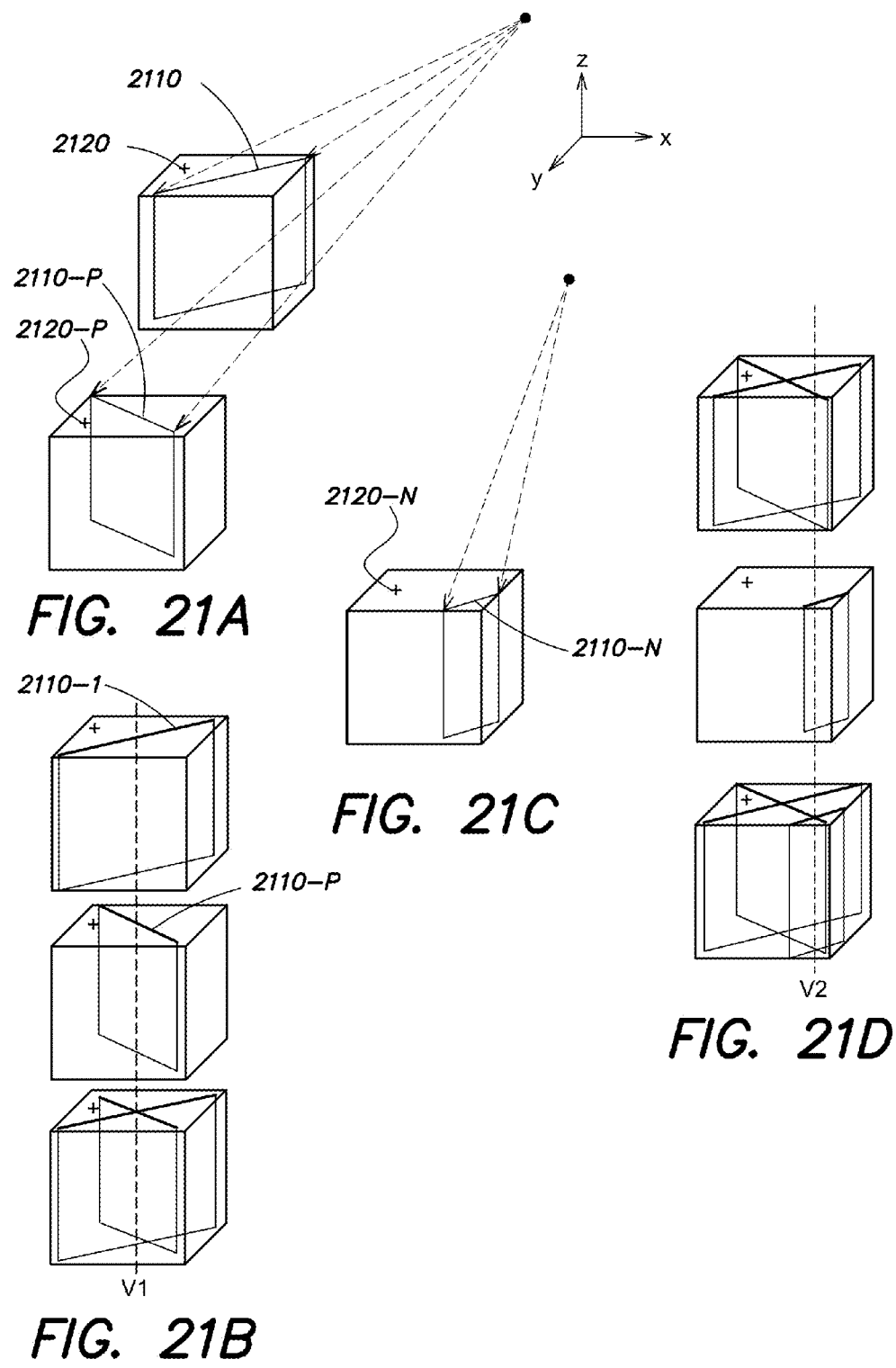
FIGS. 21A through 21D illustrate a method for 3D reconstruction of a slice scanned object with elimination of motion blur.

Implementation 2 uses a slice scan device to obtain a 3D model. This approach requires the following equipment (as depicted in FIG. 20) and operations:

1. A single two dimensional (2D) camera 2020 to capture images of the object 2020 which include at least one alignment feature on the surface of the object. The camera 2020 may be a television camera or any camera capable of capturing a sequence of images.

2. A slice scanner 2010 that measures at least the distance to the surface 2070 of the object and the distance to interior features contained within a series of slice scans (such as an OCT, CAT, Ultrasound, MRI, Sonar, Radar, or similar device).

3. The scanner is controlled 2040 such that scan slices 2060 must intersect in such a way as to create a path to travel from any single scan slice to any other scan slice.

4. A determined spatial relationship exists between the camera 2020 and slice scan device 2010. The spatial relationship may be fixed, such as by mounting the camera and the scanner on the same platform, or may change over time, as long as this spacial relationship is known.

5. The time required to scan a single slice 2060 is sufficiently fast such that no motion blur occurs during a single scan slice acquisition time or the motion blur is significantly small such that it can be ignored over the slice scan time.

6. A programmed digital computer and/or signal processor 2050, to control the camera 2020 and scanner 2010, to process the images and scans, and to perform the steps explained below. The computer/DSP 2050 may include peripherals such as storage 2052 and a display 2054 or other components not shown.

Given the above requirements are satisfied, the method of 3D object reconstruction will be described with the aid of FIGS. 21A-21D for a slice scan device such as an OCT, CAT, Ultrasound, MRI, Sonar, Radar, or similar device.

Step 1 (FIG. 21A): Take at least two slice scans, slice 1 (2110-1) and slice P (2110-P), and also capture a corresponding image of the surface with the camera; simultaneously with each scan store the slice scan and camera image data for further processing. Select at least 1 feature (2120-1, 2120-P) in the surface image of the object to be used for x and y alignment of the scanned image slices. This example uses the + sign as the alignment feature.

Step 2A (FIG. 21A): Move one surface image relative to the other surface image in x and y to overlay the alignment feature (2120-1, 2120-P). Also move the image slices relative to one another by an identical amount as the surface images, to maintain at all times the precise spatial relationship between the alignment feature on the surface image and each image slice.

Step 2B (FIG. 21B): Identify the set of scanned x, y data points and coordinates is that lie on the top surface edge of each image slice. These points will be present in the surface image of the object. These are the surface points that are closest to the imaging camera. Mathematically connect the individual scanned surface data points in each slice as shown by the bold line on the top surface of the object.

Locate the x, y data point on the top edge of each image slice that is common to both slices. This is the x, y coordinate where the two slices intersect in the x-y plane, as indicated by dashed vertical line V1.

Step 3: (FIG. 10B) Since the common x, y data point lies on the surface of the object, and since there is one and only one top surface, both slices 2110-1, 2110-P must share the same surface z value relative to the object at the surface x, y coordinate where the two slices intersect. Therefore image slice P can be connected to image slice 1 at this surface x, y, z coordinate as shown in FIG. 10B.

Step 4: (FIG. 10C) For each subsequent image slice 2110-N scanned of the object, (referred to as slice N) the alignment feature 2120-N is located in the accompanying surface image. This is true whether the object is stationary or in motion.

Step 5 (FIG. 21D): Mathematically connect the individual sampled surface data points along the top edge of Slice N using the same procedure described in step 2B.

Find which previously processed image slice number, referred to as slice P that slice N intersects. Locate the x, y coordinate that is common to scan slice N and P. This is the x, y coordinate where the two scans intersect in the x-y plane, as indicated by dashed vertical line V2.

Step 6 (FIG. 21D): At the intersecting x, y coordinate common to slices N and P (indicted by vertical line V2 in step 5) connect the two slices at the point where their top surface edges intersect such that the top edge of slice N will now have the same x, y, z coordinate value as the top edge of slice P at the intersection.

Continue operations in Steps 4, 5, and 6 until all intersecting slices have been connected where their top surface edges intersect, and construct the 3D model from the connected slices.

While FIGS. 21A to 21D illustrate the use of one alignment feature in the camera image to spatially align the object in the x,y camera plane between two slice scans. In some applications, it may be necessary or useful to use multiple features on the object surface to achieve alignment, especially if a single feature is not present in all camera images due to object motion. For slice scan application multiple features can be used to align the object in the x,y camera image plane in a similar fashion as previously explained for line scan applications. As previously explained; FIGS. 11A, 11B, and 11C show how multiple alignment features between consecutive images can be used for alignment. As an example, the "+" (plus sign) is only present in the camera image of FIG. 11A. Both the "+" sign and "*" (asterisk) are present in camera image 11B and only the "*" asterisk is present in camera image of 11C. In this example the "+" sign can be used to align FIG. 11A to FIG. 11B and the "*" asterisk can be used to align FIG. 11b to 11c. This by default aligns FIG. 11A to FIG. 11C even though they do not share a common feature. In this manner all images and scans can be aligned to each other in the x,y camera image plane. In general any one image can be aligned to any other image either by directly containing a feature common to both images or by finding pairs of common features in intermediate images linking the photos together as shown in FIGS. 11A, 11B, and 11C.

Implementation 3

Figure 22:
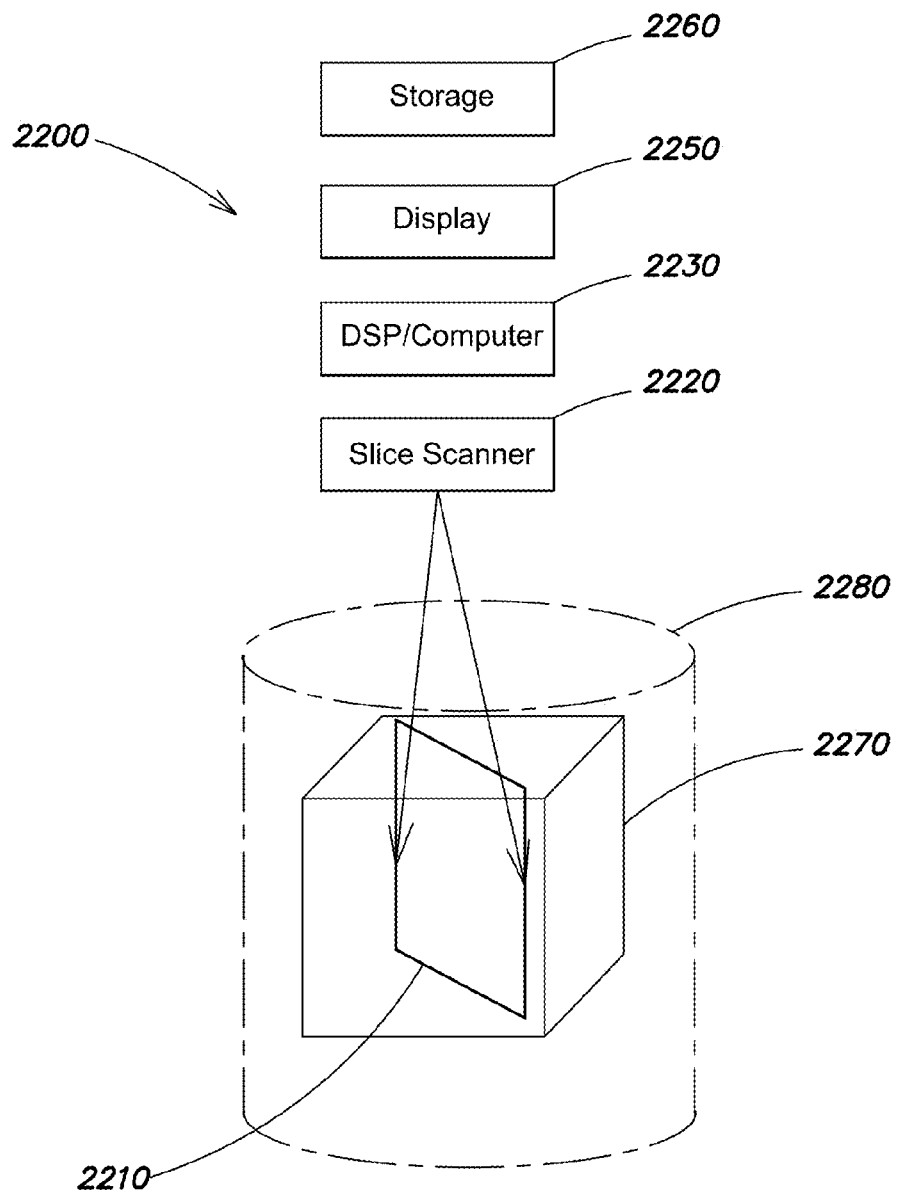
FIG. 22 represents a slice scanner without a camera.

Three Dimensional Reconstruction and Elimination of Motion Blur without the Use of a Camera and from Slice Scans of Structures Which Could be within an Object This slice scan 3D reconstruction method does not require a camera and can still reconstruct structures deep within an object such as a tumor within a body. FIG. 22 is representative of this type scanner 2200. But unlike implementation 2, which only requires that each image slice intersect at least one other slice, this implementation requires that each image slice 2210 intersect at least two other image slices.

Requirements for three dimensional reconstruction and elimination of motion blur without the use of a camera and from slice scans of structures which could be within an object are as follows:

1. Each image slice intersects at least two other image slices.

2. The image slices must intersect not only when the object 2270 in FIG. 22 is stationary but also if the object moves within a defined spatial region.

3. The image slices must intersect in such a way as to create a path to travel from any single image slice to any other image slice 4. Intersecting slices must share a common set of Intensity values along the line of intersection; referred to as the Common Intensity Vector.

5. The time required to scan a single slice is sufficiently fast such that no motion blur occurs during a single scan slice acquisition time or the motion blur is significantly small such that it can be ignored over the slice scan time.

6. A programmable digital computer or digital signal processor 2230 in FIG. 22 controls the slice scanner 2220 and processes its output, for display 2250 and/or storage 2260.

Given the above requirements are satisfied, this method of 3D object reconstruction will be described with the aid of FIGS. 22 through 34 for a slice scan device 2220 such as an OCT, CAT, Ultrasound, MRI, Sonar, Radar, or similar device. Such devices can scan the interior of objects as illustrated in FIG. 22.

FIG. 23A is an example of a radial scan pattern with intersecting scan slices. Each scan creates an image slice scan representing a two dimensional image "slice" of the object. The position of each scan slice 2210 in FIG. 22 or slice 2301, 2302, or 2303 in FIG. 23A is relative to the framework 2280 of the scanning machine and does not know where the object 2260 is positioned within the scanning field 2280. The position of the image slice corresponds to where on the object the scan slice was actually scanned, with or without object motion. Assuming that there is no object motion the relative position of each image slice 2301, 2302, 2303 with respect to the object 2300 (i.e. where each image slice was actually taken on the object at the time of scan) would look like the mechanical scan pattern shown in FIG. 23A. However, if the object moved as the different scan slices were being acquired the image slices would not intersect the object at the expected positions shown in FIG. 23A, but instead would intersect the object at the positions shown in FIG. 23B. It is important to emphasize that if the object 2300 moves during the scan, such motion is unknown, subsequently without correction, these image slices will be positioned incorrectly.

FIG. 23A thus shows the physical scan pattern and where we expect the image slices to be positioned relative to each other assuming no object motion.

FIG. 23B shows where on the object the image slices were actually acquired because the object 2300 moved while it was being scanned.

The goal of the reconstruction algorithm is to shift the scanned image slices from their expected stationary position, which does not know about object motion, to the precise location that was actually scanned on the object as it moved. Essential to the reconstruction process is the realization that intersecting image slices must share a common set of intensity values in x, y, and z along the line of intersection, as shown in FIG. 24.

Intersecting slices must share a common set of Intensity values along the line of intersection; referred to as the Common Intensity Vector. In the example of FIG. 24:

$I_{12}$=common shared intensity values between image slice 1 (2401) and image slice 2 (2402)

$I_{13}$=common shared intensity values between image slice 1 (2401) and image slice 3 (2403)

$I_{23}$=common shared intensity values between image slice 2 (2402) and image slice 3 (2403)

In some applications, the Common Intensity Vector may be composed of a large percentage of matching data points rather than requiring a 100 percent match.

For simplicity, it may be easier to explain the reconstruction process in a two dimensional space rather than in three dimensions. With this in mind FIG. 26 shows the two dimensional top view of the three dimensional model shown in FIG. 25 and the dashed lines in FIG. 26 define a spatial region 2510 over which the image slices must intersect to enable object reconstruction.

To make the reconstruction example more realistic let us begin by assuming that Image Slice 2 2402 contains two additional Intensity Vectors that have the same set of values as Common Intensity Vector $I_{23}$. The position of these duplicates $I_{23}$ are shown in FIG. 27.

The 3D reconstruction proceeds as follows:

Step 1: For each image slice 2401, 2402, 2403 find and record possible intersecting image slices within the allowable search region by looking for all matching Intensity Vectors between pairs of image slices. Record the position of the matching Intensity Vectors within each slice.

At this step in the reconstruction process how the slices are connected is not known.

Figure 28:
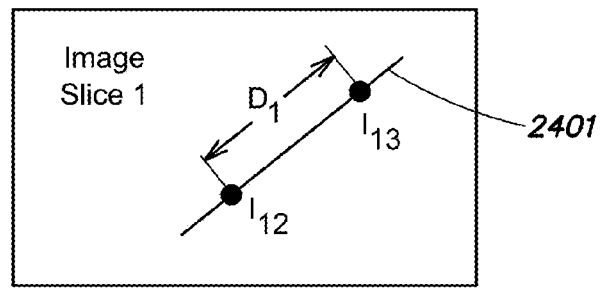
FIGS. 28, 29 and 30 show three slices and their vector intensity positions.
Figure 29:
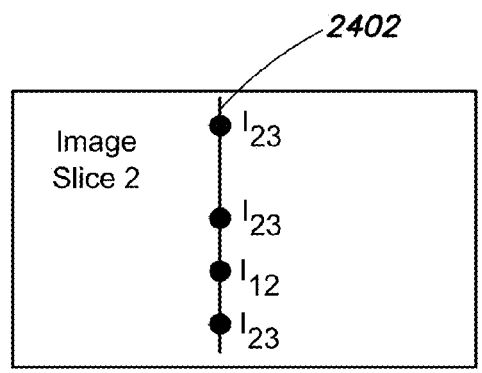
Figure 30:
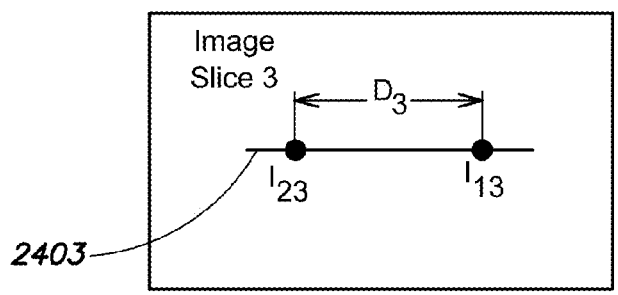
Figure 31:
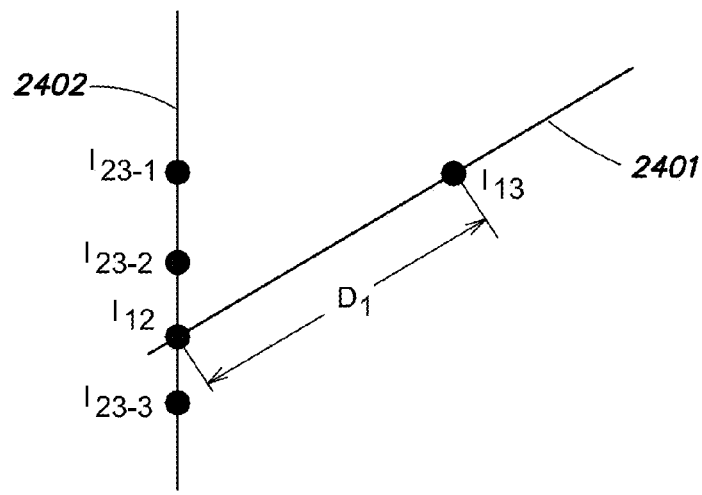
FIG. 31 shows image slice 1 and image slice 2 joined at a common vector.

What is known at this step is that there exist three slices with the Intensity Vector positions as shown in FIGS. 28, 29 and 30.

At this step in the reconstruction process, the $I_{23}$ vector position which represents the correct intersection of image slice 2 and image slice 3 is unknown.

Step 2: Reassemble the image slices and create the final model of the object such that:

1. Each pair of intersecting image slices in the scanned data must intersect in the reconstructed final model.
2. Slices in the final model must intersect such that all Intensity Vector positions within each slice are preserved and specifically the positions of the Common Vectors shared between intersecting slices.
3. If two image slices share a Common Intensity Vector and the Common Intensity Vector appears in duplicate positions within an image slice, only one of these positions can be used as the intersection between the image slices in the final model.
4. If a pair of image slices share at least two different value Common Intensity Vectors (which is not the same as the identical value in different positions of the slice), only one Common Intensity Value can be used in the final model.
5. When two intersecting image slices are connected along the line specified by a Common Vector, the intensity values in image slice 1 (2401) are aligned with the values in image slice 2 (2402) which thereby aligns the two slices in the z height axis.

Figure 32:
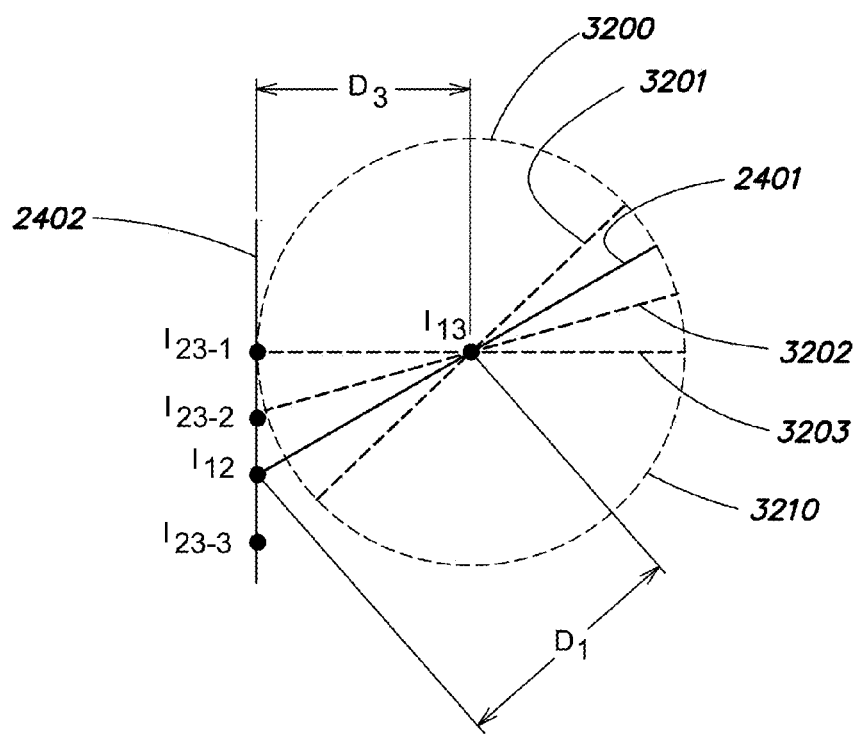
FIG. 32 shows possible positions of image slice 3 and radius $D_3$.

The rules in Step 2 are then applied to construct the final model as follows:

1. Image slices 1 and 2 are joined at Common Vector $I_{12}$—see FIG. 31.
2. There are 3 possible positions that image slice 3 (2403 in FIG. 30) can intersect image slice 2 (2402 in FIG. 29). These 3 positions are shown by dashed lines 3201, 3202 3203 in FIG. 32. The positions are: $I_{23-1}$, $I_{23-2}$, $I_{23-3}$. According to Step 2 only one of these three possible positions can be used in the final model and all intersecting slices in the acquired data must be used in the final model. To determine the correct intersection: Image Slice 3 (2403 in FIG. 30) is first joined to slice 1 in FIG. 28 at Common Vector $I_{13}$. We know from the image slice acquired from the scan that the distance between Vector $I_{13}$ and $I_{23}$ in slice 3 is $D_3$ as shown in FIG. 30. If we draw a circle 3200 of radius $D_3$ around vector $I_{13}$, as shown in FIG. 32, we see that $I_{23-1}$ is the only position that can be connected, and is therefore chosen as the correct intersection of image slices 2 and 3. In other words, only $I_{23-1}$ in image slice 2 (2402 in FIG. 32) can intersect image slice 3 (3202 in FIG. 32) for the distance between $I_{13}$ and $I_{23}$ equal to $D_3$. See FIG. 33. In general, as the number of intersecting image scans and corresponding image slices increase, this imposes more spatial constraints which helps lock in the correct placement of all the slices.

While the example above compensates for translational motion, the algorithm can also compensate for rotational motion by searching for Common Vectors along diagonals. Furthermore, additional system and object information can be extrapolated from the measured parameters to indicate where to begin looking for the slice intersections.

Figure 34A:
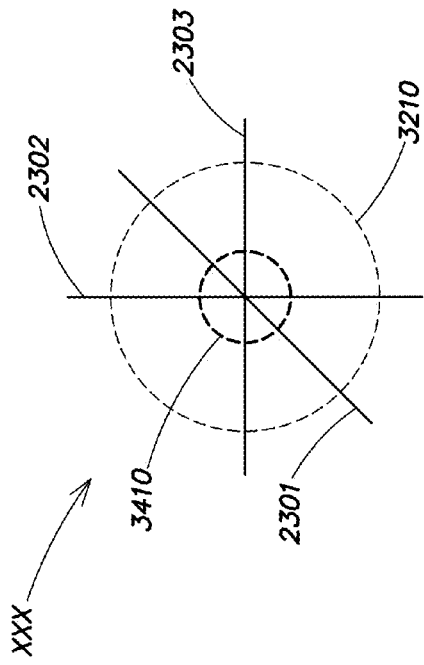
FIG. 34A is a mechanical scan pattern and FIG. 34B the corresponding intersecting slices.
Figure 34B:
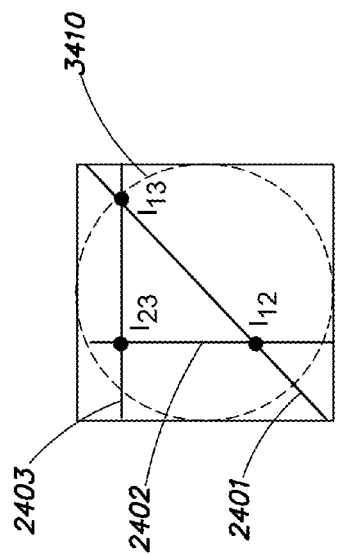
FIG. 34C shows how a larger region can be scanned by four smaller intersecting regions.
Figure 33:
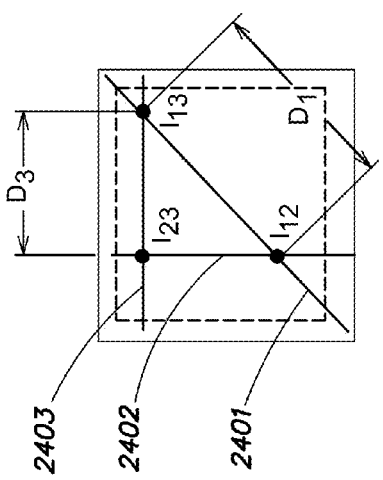
FIG. 33 is a final reconstructed model.

This information includes:

1. Knowledge of the system mechanical slice scan angle and mechanical slice position, as shown in FIGS. 34A and 34B.
2. Maximum rate of object motion between slices Assuming:
   i. The first scan of the object is image slice 1 (scan slice 1=image slice 1) and consecutive temporal and spatial slices of the object are taken every N seconds; and
   ii. The maximum rate of object motion is M millimeters/second.

Then the maximum search area for temporal slice 2 relative to scan slice 1 is a sphere of radius M mm/sec×Nsec.

b. For each consecutive scan, knowledge of the physical scan angle and scan position (FIG. 34A) combined with the maximum rate of object motion can be used to limit the search area (between the inner radius circle 3410 and outer circle 3210). (Is this correct?)

It is important to emphasize that once the first few image slices (3 or 4 for example) have been connected at their correct Common Vector positions, this information limits the search area 3410 for the next consecutively acquired image slice.

Figure 34C:
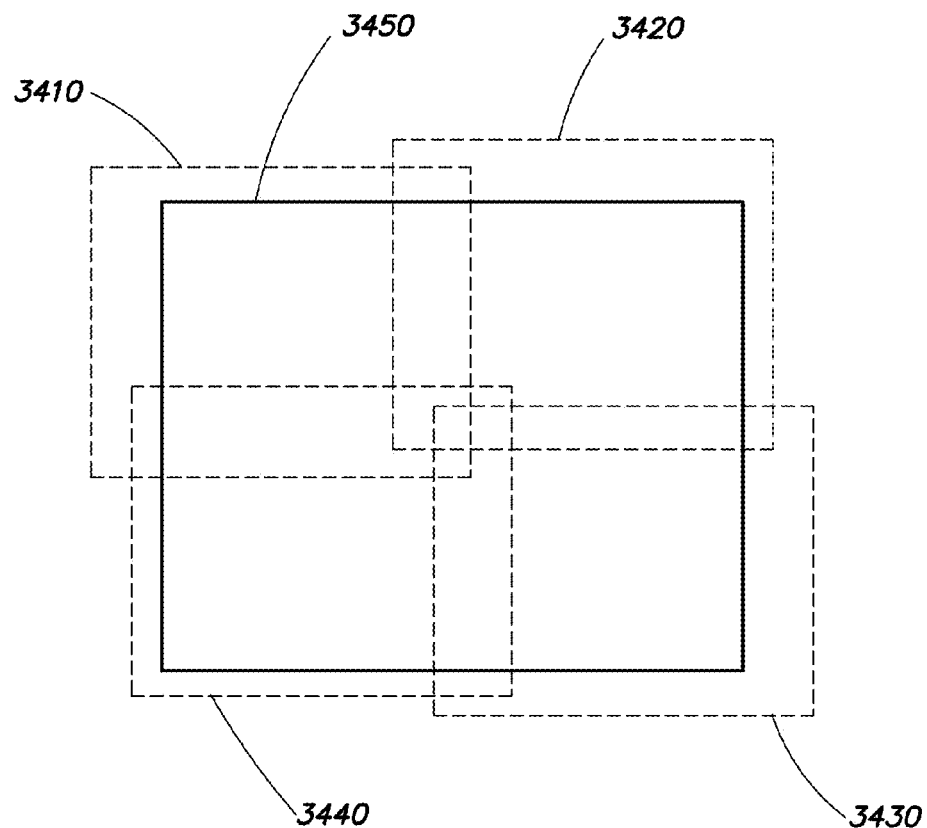

Another major feature of this reconstruction algorithm is that in the event that motion blur occurs during acquisition of a slice scan, this blur can be reduced or eliminated. This can be accomplished by reducing the area and time of each scan and increasing the total number of intersecting slices scanned within the object. In other words, the size of each scan slice is adjusted to eliminate or minimize motion blur over the scan slice acquisition time. As an example: FIG. 34C illustrates how the larger region scanned by slice 3450 can be scanned by the 4 smaller intersecting regions 34100, 34200, 34300, and 34400. In this example the time required to scan each of the smaller regions is approximately one quarter the time required to scan larger region 3450, which thereby reduces any motion blur.

Combining Three Dimensional Sub-Sections to Create the Entire Model

Figure 35:
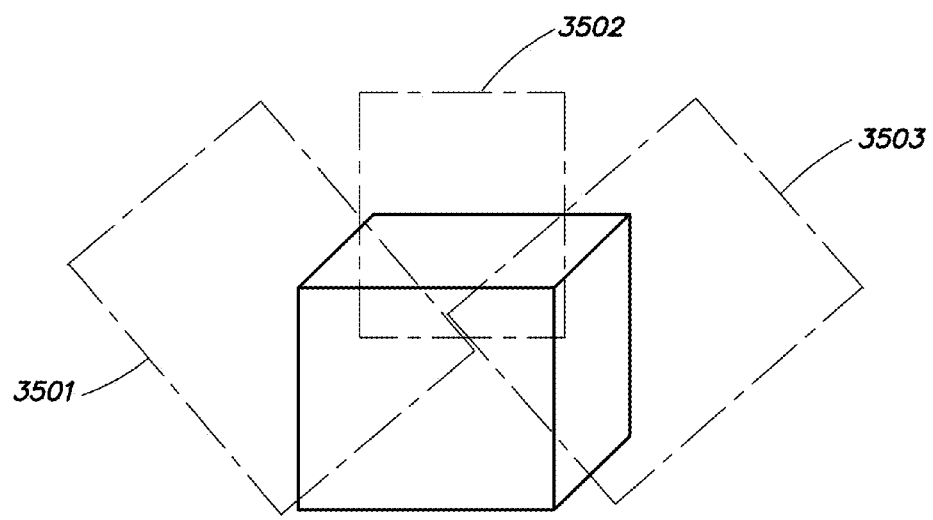
FIG. 35 shows an object being scanned from different angles.

To obtain access to all object surfaces it is frequently necessary to scan an object from different angles 3501, 3502, 3503 as shown in FIG. 35.

Figure 36:
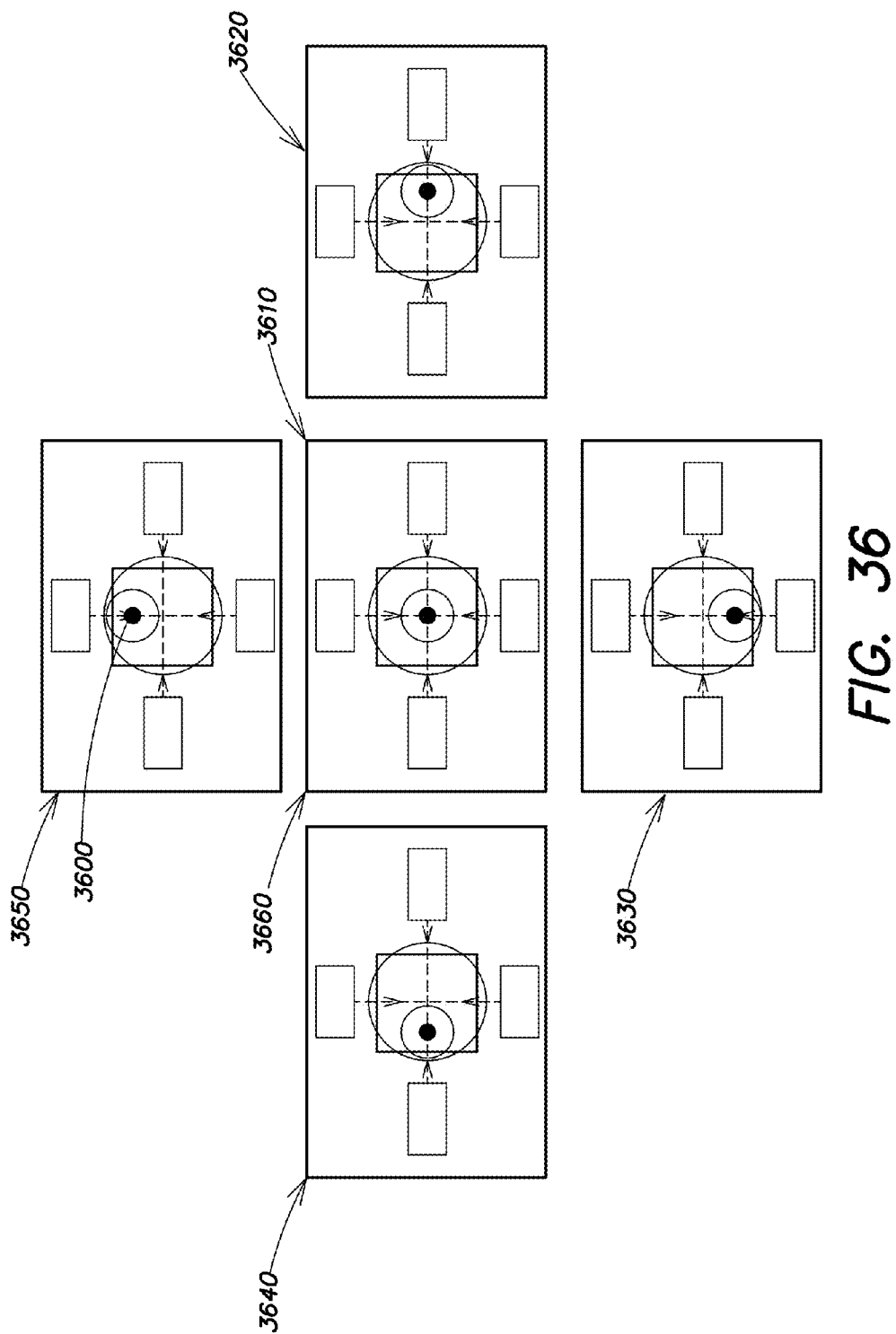
FIG. 36 is an example of taking images for different gazes of the eye.

As an example, to create a three dimensional model of the eye which includes the regions of the sclera normally covered by the eyelids it is often necessary to combine multiple scans taken with the eye 3600 at different orientations or gazes (3610, 3620, 3630, 3640, 3650, 3660) as shown in FIG. 36. An algorithm for stitching together sub-sections of the same object taken at different orientations or different gazes to create an entire 3D model is now described in connection with FIGS. 37 through 42.

Figure 37:
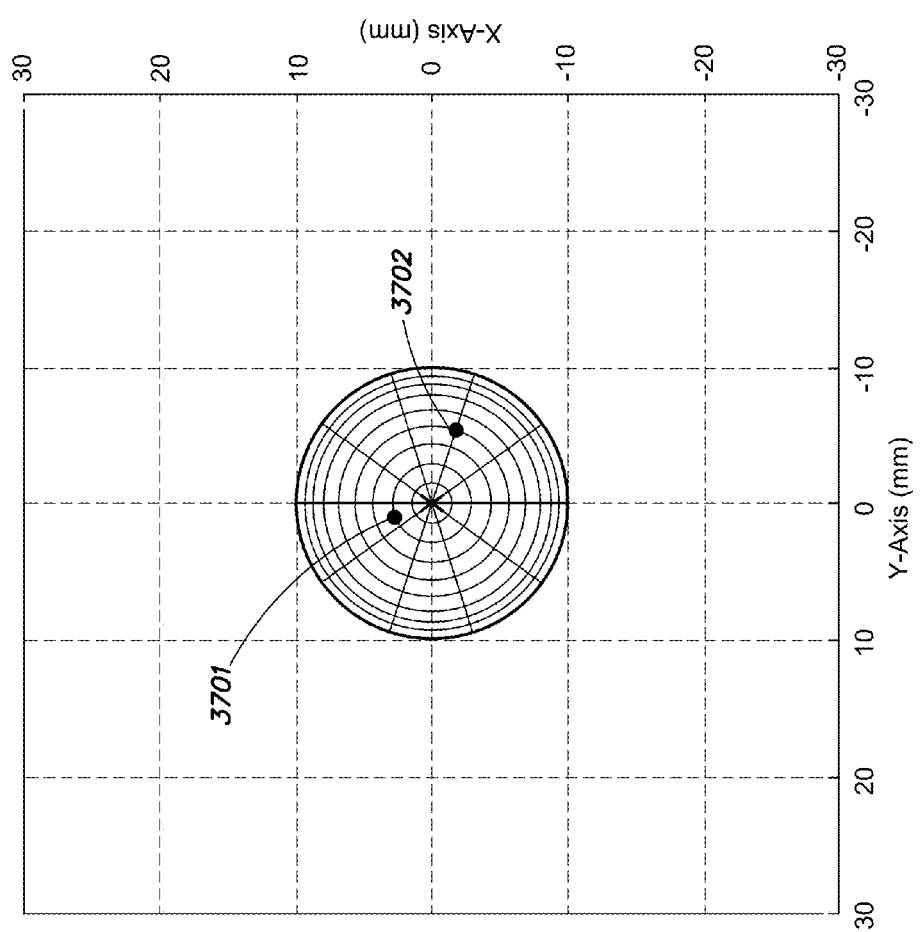
FIG. 37 is a head on view of an object with two alignment features.

FIG. 37 is the head on view of an object with two alignment features shown as two dots 3701, 3702.

To stitch together multiple sub sections—perform the following steps:

Step 1 (FIG. 37): Given two 3D sections from the same object that are to be aligned: Select at least two alignment features (3701, 3702) present in the camera image of each 3D section and find the x,y centroid of each feature in each camera image. Each camera image must contain both alignment features as illustrated in FIG. 37. Use the x,y centroid position to extract its z position from the 3D model section.

Figure 38:
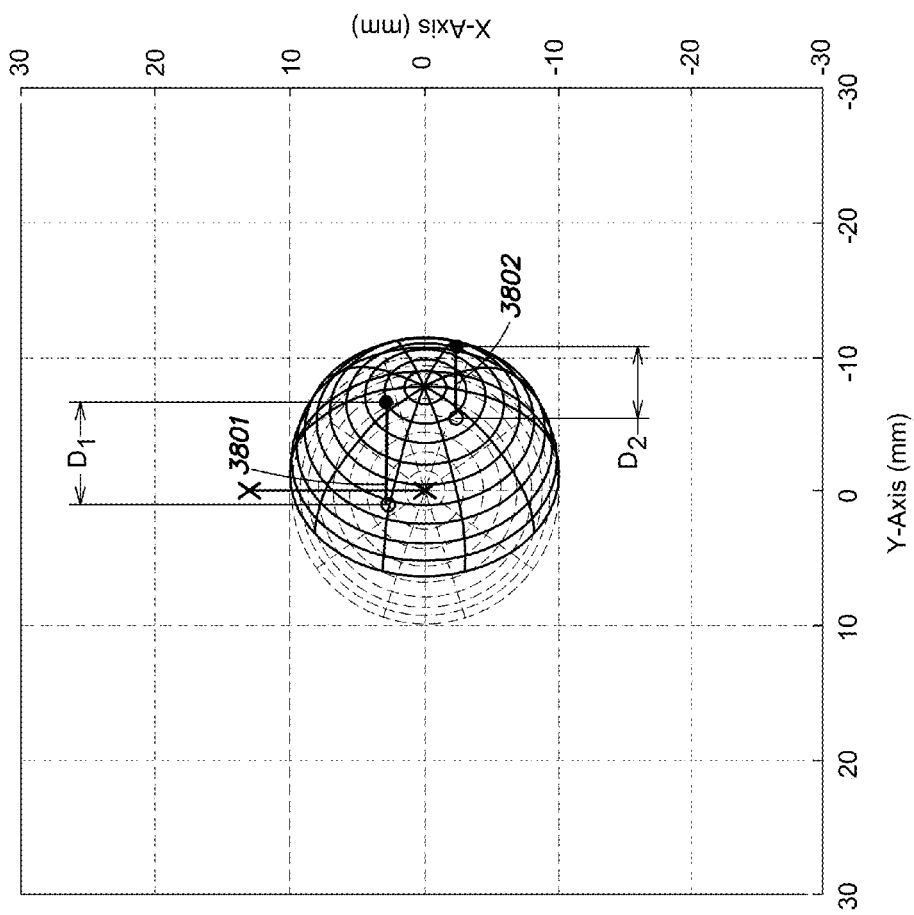
FIG. 38 shows how to locate alignment features in object models.

Step 2 (FIG. 38): Locate the corresponding alignment features in both 3D sections of the object. In FIG. 38, the dashed lines with hollow dots show object section 1, and the solid lines with solid dots show rotated object section 2.

Vector A (3801) of Length=D1 and Vector B (3802) of Length=D2 represent the difference in position of the same alignment features between the two sections. i(Note also that in this example that D1>D2).

Step 3a (FIG. 39): Prepare for Translation

Figure 39:
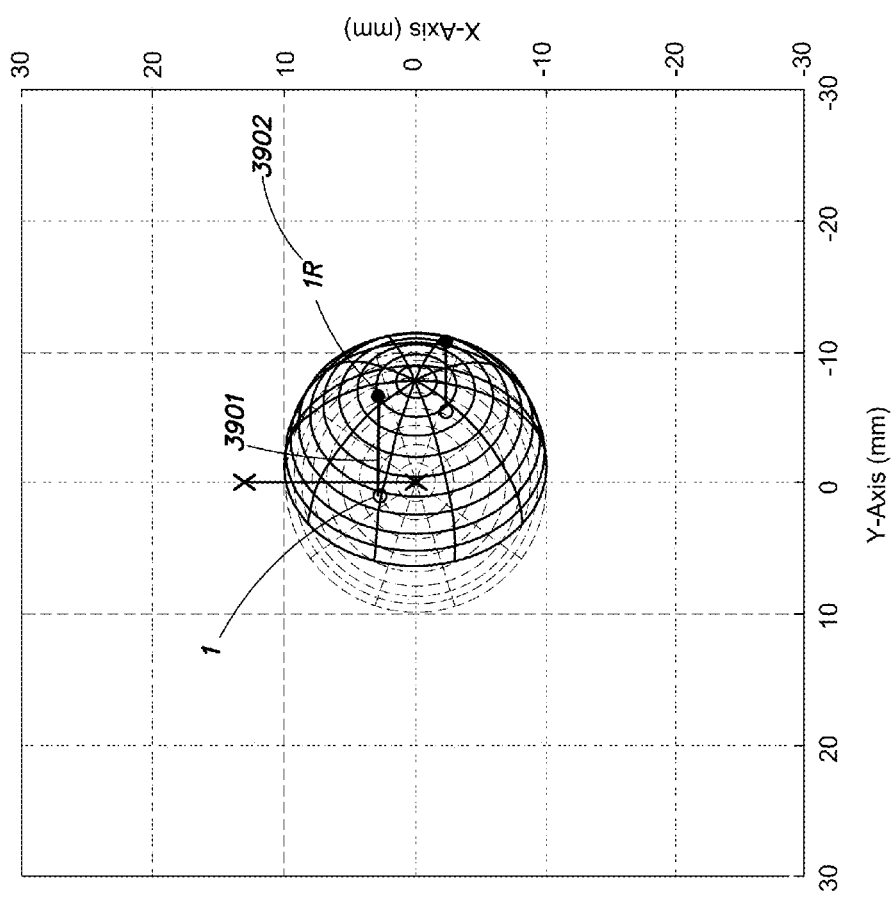
FIG. 39 illustrates preparation for translation correction.

FIG. 39 shows the spatial relationship prior to translation. In FIG. 39, the dashed lines with hollow dots show object section 1, and the solid lines with solid dots show rotated 1 object section 2.

In this step, we select Vector A (3901) for translation of the first alignment feature. We then translate the model of section 2 along Vector A such that Feature 1R (3902) has the same X,Y,Z Coordinate as Feature 1.

Step 3b (FIG. 40): This figure shows the spatial relationship of the two models after the translation operation described in Step 3a.

Figure 40:
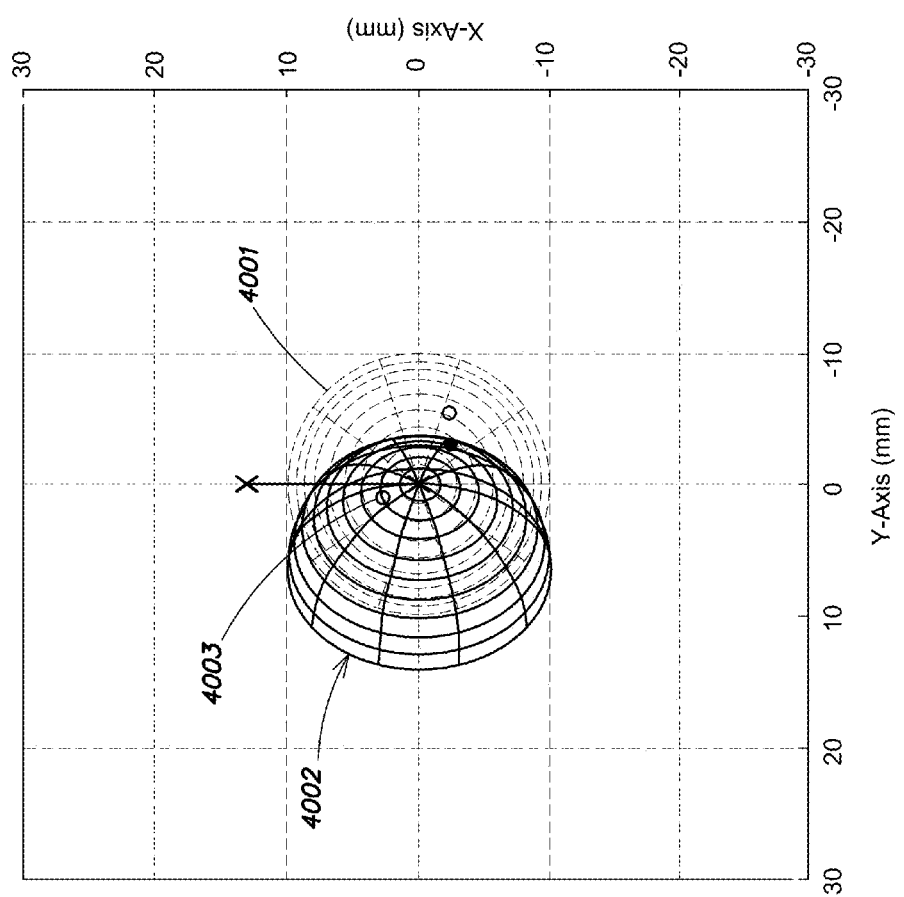
FIG. 40 illustrates a spatial relationship of the two models after translation.

In FIG. 40, the dashed line image 4001 is the original position of 3D object section 1.

The solid lines 4002 represent the position of the rotated object section after Feature 1R (3902 in FIG. 39) in 3D object section 2 has been superimposed over Feature 1 in 3D object section 1 of FIG. 40.

Step 4a (FIG. 41): Prepare for Rotation Correction.

Figure 41:
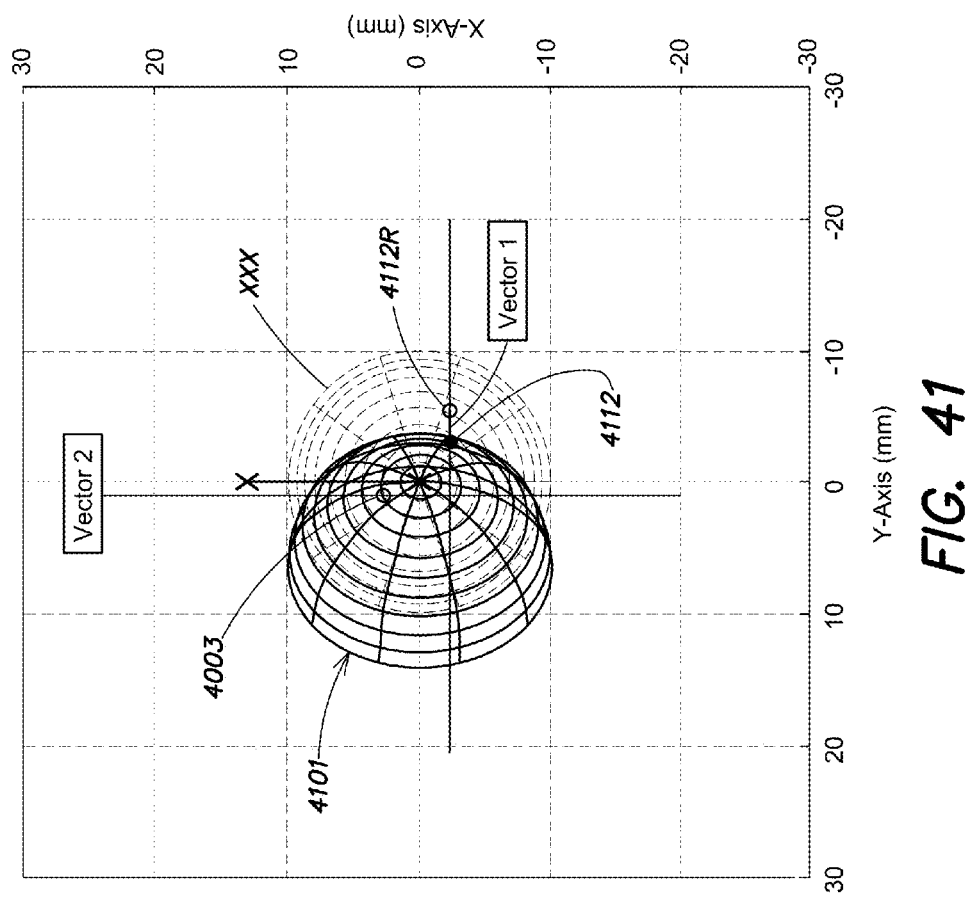
FIG. 41 illustrates preparation for rotation correction.

FIG. 41 shows the Solid Line object section 4101 including aligned feature 4003 prior to rotation.

To correct for rotation, we define Vector 1 as the line that passes through the two similar but unaligned Features 2 (4112) and 2R (4112R) in the X,Y Plane.

We then define Vector 2 as the line that passes through the aligned feature 4003 in X, Y and Z and is perpendicular to Vector 1.

To correct for rotation, we rotate the entire model (solid lines) around Vector 2 until the two unaligned features 2 and 2R (4112 and 4112R, respectfully) share the same X, Y, Z position.

Step 4b (FIG. 42): Perform the rotation operation described in Step 4a.

Figure 42:
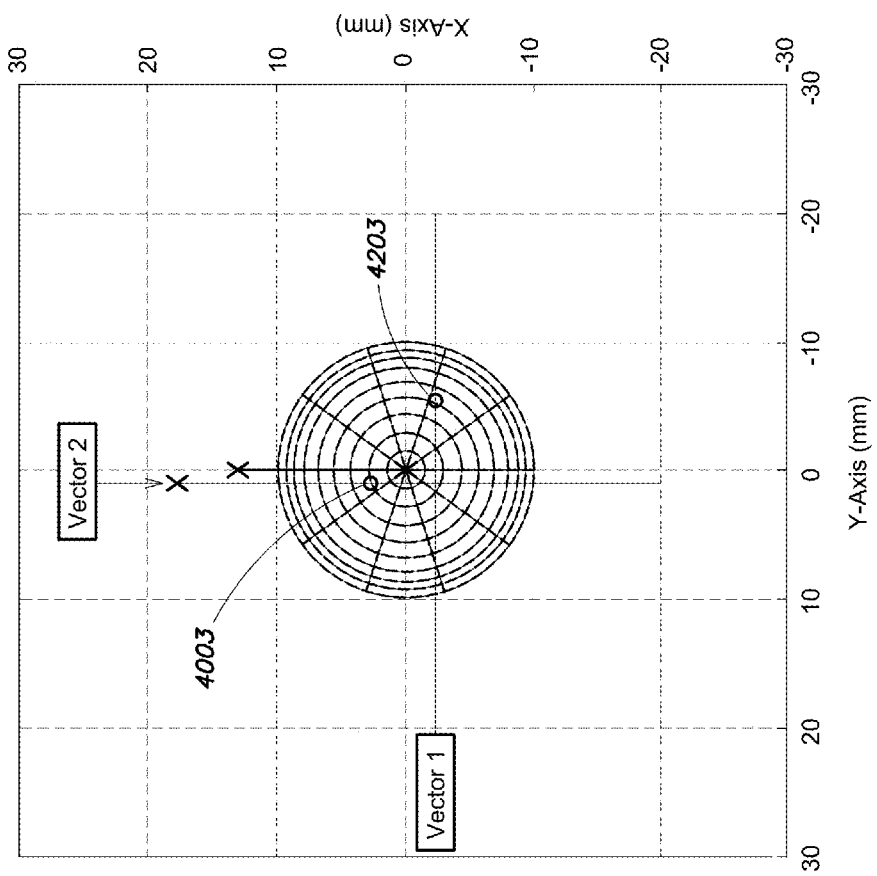
FIG. 42 shows rotation correction.

FIG. 42 shows Feature 1 superimposed over feature 1R (4003) and Feature 2 superimposed (4203) over Feature 2R.

After the Rotation Operation is complete, all features and the two models are aligned in X, Y and Z, as shown in FIG. 42.

Figure 43B:
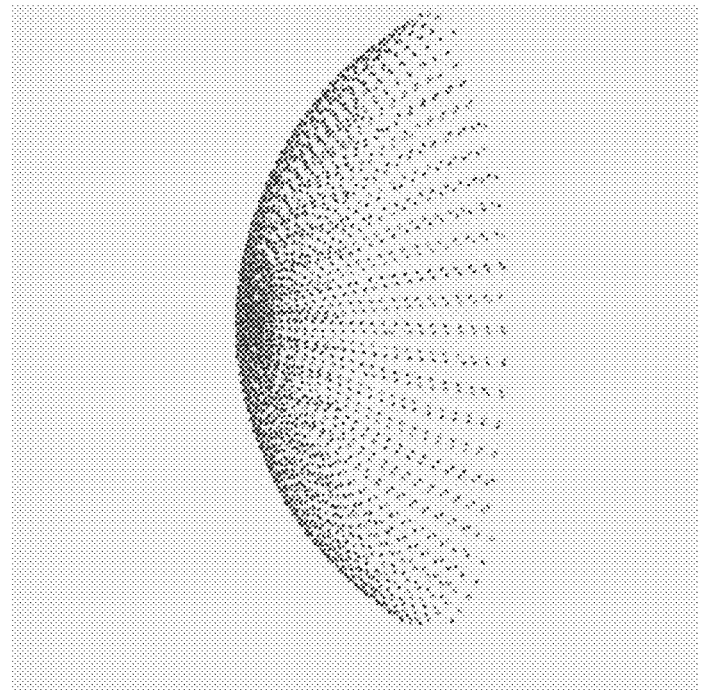
FIGS. 43A and 43B illustrate, respectively, the result of scanning without and then with the correction techniques.
Figure 43A:
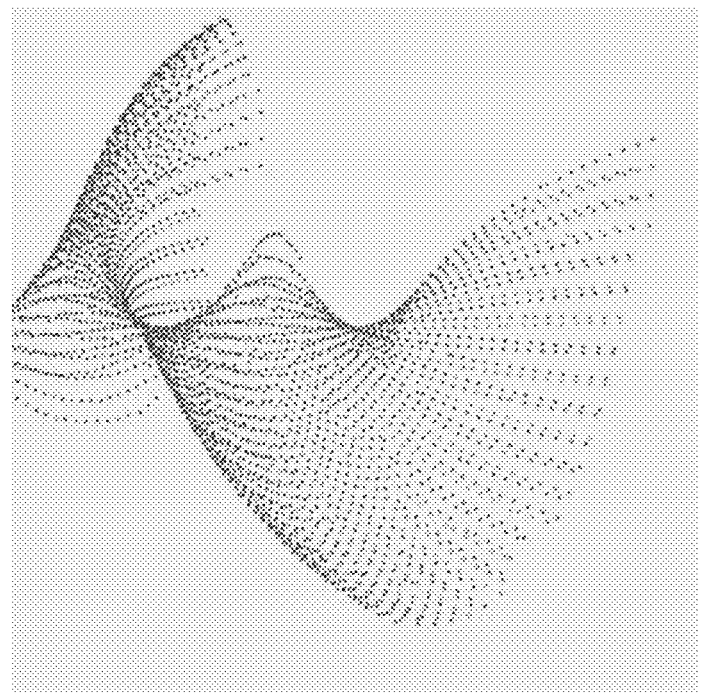

An improvement possible with the techniques described herein became evident with a simple test. First, a spherical object having a red dot as a reference feature was scanned using a line scanner. The sphere was moved away from the scanner in a direction perpendicular to the front of the scanner as the sequence of meridian scans were taken. The total distanced the sphere moved during the scan was 15 millimeters. The system was not given any information about the path of the sphere. FIG. 43A is the result when only the meridian scans are used; note the disarray of the resulting points.

Next, we scanned the same sphere with red dot again, but this time we also captured a picture simultaneously with each meridian scan. We also ran the line scan algorithm as described above in connection with FIGS. 10A-10D using the red dot as the reference feature. The system was again given no other information about the path of the sphere and again the total distance the sphere moved during the scan was 15 millimeters. FIG. 43B was the result—demonstrating a marked improvement in the ability to correctly detect the detailed shape of the sphere, even as the sphere is moving with respect to the camera.

What is claimed is:

1. An apparatus for generating a three dimensional representation of an object, the object having at least one distinct visual feature, the apparatus comprising:
   A) a camera directed along an imaging axis for generating a sequence of two-dimensional images of the object in which each camera image contains at least one of the distinct visual feature or features,
   B) a scanner for generating scans, each scan including a plurality of sampled measurements of the object,
   C) a platform for maintaining a determined spatial relationship between the scanner and the camera,
   D) a control connected to said camera and said scanner, the control:
   i) controlling the scanner to produce a plurality of scan lines, each scan line including a plurality of sampled measurements, each of the scan lines intersecting at least one other scan line in an image plane observed by the camera, to thereby create a path from any single scan line to any other scan line in the image plane,
   ii) capturing an image of the object including at least one distinct visual feature from the camera for each of the plurality of scan lines, thereby capturing a corresponding camera image for each scan line,
   iii) aligning the camera images by overlaying the distinct visual feature or features shared by the camera images,
   to thereby also align the corresponding scan lines in the image plane by a corresponding amount,
   iv) connecting the individual sampled measurements for each given scan line to produce a continuous representation of each scan line in three dimensional space, and
   v) for at least one set of two scan lines,
      (i) locating a point in the image plane where the continuous representations of the two scan lines cross, and
      (ii) moving at least one scan line along the imaging axis in a plane perpendicular to the image plane so that the two continuous scan line representations intersect at a common point in three dimensional space, thereby compensating for movement of the object between successive scans of the scanner.

2. The apparatus of claim 1 where the control is further for aligning the camera images by ensuring that any one camera image can be aligned to at least one other camera image by the camera images either sharing at least one distinct feature directly in common with another camera image or by sharing at least one feature in common with an intermediate camera image which has been aligned to a previous camera image.

3. The apparatus of claim 1 wherein the control is further for generating the three dimensional representation of the object from two or more of the continuous scan line representations.

4. The apparatus of claim 1 wherein the captured image is a two-dimensional image of a surface of the object containing at least one distinct visual feature.

5. The apparatus of claim 1 wherein the scanner is a surface height scanner and the sampled measurements each correspond to a height determined from a distance between a reference point to the object at a selected position along the scan line.

6. The apparatus of claim 1 wherein the line scanner is one of a triangulation sensor, sonar or radar unit.

7. The apparatus of claim 1 wherein a time to acquire the sampled measurements is sufficiently small such that motion blur occurring during the sampling of a scan line can be ignored.

8. An apparatus for generating a three dimensional representation of an object, the object having at least one distinct visual feature, the apparatus comprising:
   A) a camera directed along an imaging axis for generating a sequence of two-dimensional images of the object in which each camera image contains at least one distinct visual feature or features,
   B) a scanner for generating scans, each scan including a plurality of sampled measurements of the object,
   C) a platform for maintaining a determined spatial relationship between the scanner and the camera, D) a control connected to said camera and said scanner, the control:
- i) controlling the scanner to produce a plurality of scan slices, each scan slice including a plurality of sampled measurements, each of the scan slices intersecting at least one other scan slice in an image plane observed by the camera, to thereby create a path from any single scan slice to any other scan slice in the image plane,
- ii) capturing an image of the object including at least one distinct visual feature from the camera for each of the plurality of scan slices, thereby capturing a corresponding camera image for each scan slice,
- iii) ensuring that any one camera image can be aligned to at least one other camera image either by sharing at least one distinct feature directly in common with another camera image or by sharing at least one feature in common with an intermediate camera image which has been aligned to a previous camera image
- iv) aligning the captured camera images by overlaying the distinct visual feature or features shared by the camera images, to thereby also align the corresponding scan slices in the image plane by a corresponding amount,
- v) extracting the surface of the object from each slice scan, and connecting the individual sampled surface measurements in the slice scan to produce a continuous representation of the object surface referred to as a surface line
- vi) for at least one set of two object surface lines,
    - (i) locating a point in the image plane where the continuous representations of the two surface lines cross, and
    - (ii) moving at least one surface line with its corresponding slice scan along the imaging axis in a plane perpendicular to the image plane so that the two continuous surface line representations intersect at a common point in three dimensional space, thereby compensating for movement of the object between successive slice scans of the scanner.

9. The apparatus of claim 8 wherein the control is further for generating the three dimensional representation of the object from two or more of the scan slices.

10. The apparatus of claim 8 wherein the captured image is a two-dimensional image of a surface of the object containing at least 1 distinct visual feature.

11. The apparatus of claim 8 wherein the scanner is a two or three dimensional scanner and the sampled measurements each correspond to the intensity of a returned signal from an object measured at a specific x,y or x,y,z coordinate in the scanner.

12. The apparatus of claim 8 wherein the slice scanner is one of an OCT, CAT, Ultrasound, MRI, sonar, or radar.

13. The apparatus of claim 8 wherein a time to acquire the sampled measurements is sufficiently small such that motion blur occurring during the sampling of a scan slice can be ignored.

14. An apparatus for generating a three dimensional representation of an object, the apparatus comprising:
- A) a scanner for generating slice scans, each slice scan including an array of samples in two dimensions, each sample representing an intensity of a detected physical property of the object,
- B) a control connected to said scanner, the control:
    - i) controlling the scanner to produce a plurality of slice scans, the slice scans arranged such that each slice scan intersects at least two other slice scans, even as the object moves between successive slice scans, and the slice scans also intersecting such that a continuous path exists from each slice scan to any other slice scan,
    - ii) locating a set of common intensity values that a given scan slice has in common with a selected intersecting slice, and
    - iii) aligning the intensity values that the given slice and selected intersecting slice have in common, to thereby fix a position for the given scan slice and selected intersecting slice in the three dimensional representation of the object.

15. The apparatus of claim 14 wherein the control is further for:
- iv) locating two or more sets of common intensity values that the given slice has in common with the selected slice,
- v) using relative position information for the given slice with respect to a third slice to determine which one of the two or more sets of common intensity values to use to fix the position of the given scan slice and the selected intersecting slice.

16. The apparatus of claim 14 wherein the control is further for:
limiting a size and location of a search area within which to locate intersecting slices using (a) slice scan angle and slice position and (b) a known maximum rate of object motion between scan slices.

17. The apparatus of claim 14 wherein a time to acquire the samples is sufficiently small such that motion blur occurring during successive samples of a slice scan can be ignored.

18. The apparatus of claim 14 wherein the slice scanner is one of a OCT, CAT, Ultrasound, MRI, sonar, or radar.

19. The apparatus of claim 14 wherein the control is further for adjusting the size of each scan slice to eliminate or minimize motion blur over the scan slice acquisition time.

20. The apparatus of claim 8 wherein the control is further for adjusting the size of each scan slice to eliminate or minimize motion blur over the scan slice acquisition time.

* * * * *

UNITED STATES PATENT AND TRADEMARK OFFICE
CERTIFICATE OF CORRECTION

| | |
|---|---|
| PATENT NO. | : 9,489,753 B1 |
| APPLICATION NO. | : 15/213709 |
| DATED | : November 8, 2016 |
| INVENTOR(S) | : Robert P. Bishop et al. |

It is certified that error appears in the above-identified patent and that said Letters Patent is hereby corrected as shown below:

On the Title Page, first column, the Assignee should be corrected as follows:

--(73)   Assignee: Image Recognition Technology, LLC,
             Needham, MA (US)--

Signed and Sealed this
Twenty-ninth Day of November, 2016

Michelle K. Lee
*Director of the United States Patent and Trademark Office*